US012611443B2

(12) United States Patent
Becker et al.

(10) Patent No.: US 12,611,443 B2
(45) Date of Patent: Apr. 28, 2026

(54) METHODS AND COMPOSITIONS RELATED TO THERAPEUTIC PEPTIDES FOR CANCER THERAPY

(71) Applicant: THE UNIVERSITY OF CHICAGO, Chicago (IL)

(72) Inventors: Lev Becker, Chicago, IL (US); Chang Cui, Chicago, IL (US)

(73) Assignee: THE UNIVERSITY OF CHICAGO

( * ) Notice: Subject to any disclaimer, the term of this patent is extended or adjusted under 35 U.S.C. 154(b) by 1031 days.

(21) Appl. No.: 17/346,480

(22) Filed: Jun. 14, 2021

(65) Prior Publication Data

US 2022/0000977 A1 Jan. 6, 2022

Related U.S. Application Data

(63) Continuation of application No. PCT/US2019/067890, filed on Dec. 20, 2019.

(60) Provisional application No. 62/782,690, filed on Dec. 20, 2018.

(51) Int. Cl.

| | |
|---|---|
| ***A61K 38/17*** | (2006.01) |
| ***A61K 38/48*** | (2006.01) |
| ***A61K 39/00*** | (2006.01) |
| ***A61P 35/00*** | (2006.01) |

(52) U.S. Cl.

CPC ........ *A61K 38/1793* (2013.01); *A61K 38/486* (2013.01); *A61K 39/0011* (2013.01); *A61P 35/00* (2018.01)

(58) Field of Classification Search

CPC .............. A61K 38/1793; A61K 38/486; A61K 9/0019; A61K 9/127; A61K 39/0011; A61K 45/06; A61K 38/177; A61P 35/00; C07K 14/70578; C12Y 304/21037

See application file for complete search history.

(56) References Cited

U.S. PATENT DOCUMENTS

| | | | |
|---|---|---|---|
| 9,850,308 | B2 | 12/2017 | Martin-Villalba et al. |
| 2012/0183552 | A1 | 7/2012 | Joseloff et al. |
| 2015/0306196 | A1 | 10/2015 | Zeng |
| 2016/0121001 | A1 | 5/2016 | Leubitz et al. |
| 2018/0169189 | A1 | 6/2018 | Pule et al. |

FOREIGN PATENT DOCUMENTS

| | | |
|---|---|---|
| WO | WO 2000/069897 | 11/2000 |
| WO | WO 2008/067305 | 6/2008 |
| WO | WO 2014/060848 | 4/2014 |
| WO | WO 2014/118643 | 8/2014 |
| WO | WO 2016/166521 | 10/2016 |
| WO | WO 2018/073394 | 4/2018 |
| WO | WO 2018/232273 | 12/2018 |
| WO | WO 2019/051001 | 3/2019 |

OTHER PUBLICATIONS

Bruno et al [Ther Deliv, Nov. 2013, 4(11), 1443-1467] (Year: 2013).*

Bowie et al (Science, 1990, 247:1306-1310) (Year: 1990).*

Burgess et al (J. Cell Biol. 111:2129-2138, 1990) (Year: 1990).*

Lazar et al (Mol. Cell. Biol., 8:1247-1252, 1988) (Year: 1988).*

Chen et al., "CD95 promotes tumour growth" Nature 2010, 465(7297), 492-496.

Extended European Search Report issued in Corresponding European Application No. 19899959.1, dated Jul. 21, 2022.

Raghava et al., "Quantification of the variation in percentage identity for protein sequence alignments" *BMC Bioinformatics* 2006, 7:415, 4 pages.

Office Action issued in corresponding Chinese Application No. 201980092976.7, dated Aug. 26, 2023.

Chen et al., "Sugar transporters for intercellular exchange and nutrition of pathogens" *Nature* 2010, 468, 527-532.

Coffelt et al., "IL-17-producing γδ T cells and neutrophils conspire to promote breast cancer metastasis" *Nature* 2015, 522, 345-348.

Coffelt et al., "Neutrophils in cancer: neutral no more" *Nature Reviews Cancer* 2016, 16, 431-446.

Dancey et al., "Neutrophil kinetics in man." *J Clin Invest.* 1976, 58(3), 705-715.

Eruslanov et al., "Mouse versus Human Neutrophils in Cancer: A Major Knowledge Gap" *Trends in Cancer* 2017, 3(2), 149-160.

Finisguerra et al., "MET is required for the recruitment of anti-tumoural neutrophils" *Nature* 2015, 522, 349-353.

Hadji et al., "Death Induced by CD95 or CD95 Ligand Elimination" *Cell Rep.* 2014, 7, 208-222.

Houghton et al., "Neutrophil Elastase-Mediated Degradation of IRS-1 Accelerates Lung Tumor Growth" *Nat Med.* 2010, 16(2), 219-223.

International Search Report and Written Opinion issued in Corresponding PCT Application No. PCT/US2019/067890, dated Mar. 24, 2020.

Kruger et al., "Neutrophils: Between Host Defence, Immune Modulation, and Tissue Injury" *PLoS Pathog.* 2015, 23 pages.

Martin-Villalba et al., "CD95 in cancer: tool or target?" *Trends Mol Med.* 2013, 19(6), 329-335.

Murmann et al., "Induction of DISE in ovarian cancer cells in vivo" *Oncotarget* 2017, 8(49), 84643-84658.

Nathan, C. "Neutrophils and immunity: challenges and opportunities" *Nat Rev Immunol.* 2006, 6, 173-182.

Ngwa et al., "Using immunotherapy to boost the abscopal effect" *Nature Reviews Cancer* 2018, 18, 313-322.

Peter et al. "The role of CD95 and CD95 ligand in cancer," *Cell Death & Differentiation* 2015, 22(4), 549-559.

Pham, Christine T. N. "Neutrophil serine proteases: specific regulators of inflammation" *Nat Rev Immunol.*, 2006, 6, 541-550.

(Continued)

*Primary Examiner* — Sudhakar Katakam

(74) *Attorney, Agent, or Firm* — Norton Rose Fulbright US LLP

(57) ABSTRACT

Embodiments of the current invention provide a solution to the problems associated with balancing patient toxicity with broad efficacy of cancer therapy. In particular, embodiments are directed to anti-cancer peptides that demonstrate a broad anti-cancer efficacy with a limited toxicity to normal or non-cancer cells.

6 Claims, 9 Drawing Sheets

Specification includes a Sequence Listing.

(56) References Cited

OTHER PUBLICATIONS

Powell et al., "Neutrophils in the Tumor Microenvironment" *Trends in Immunology* 2016, 37(1), 41-52.
Sagiv et al., "Phenotypic Diversity and Plasticity in Circulating Neutrophil Subpopulations in Cancer" *Cell Reports* 2015, 10, 562-573.
Shen et al., "Tumor-Associated Neutrophils as a New Prognostic Factor in Cancer: A Systematic Review and Meta-Analysis" *PLoS One* 2014, 9(6): e98259, 10 pages.
Strand et al., "Cleavage of CD95 by matrix metalloproteinase-7 induces apoptosis resistance in tumour cells" *Oncogene* 2004, 23, 3732-3736.
Yan et al., "Human polymorphonuclear neutrophils specifically recognize and kill cancerous cells" *OncoImmunology* 2014, 3:7, e950163, 9 pages.
Young et al., "Mechanism of membrane damage mediated by human eosinophil cationic protein" *Nature* 1986, 321, 613-616.
Choi et al., "Predicting the Functional Effect of Amino Acid Substitutions and Indels," Plos One, 7(10):e46688, pp. 1-13, 2012.
Dehouck et al., "Fast and accurate predictions of protein stability changes upon mutations using statistical potentials and neural networks: PoPMuSiC-2.0," BioInformatics, 25(19)2537-2543, 2009.
Guo et al., "Protein tolerance to random amino acid change," PNAS, 101(25):9205-9210, 2004.
Matthews, "Structural and Genetic Analysis of Protein Stability," Annu. Rev. Biochem., 62:139-60, 1993.
Ng and Henikoff, "Predicting the Effects of Amino Acid Substitutions on Protein Function," Annu. Rev. Genomics. Hum. Genet., 7:61-80, 2006.
Teng et al., "Sequence feature-based prediction of protein stability changes upon amino acid substitutions," BMC Genomics, 11(Suppl. 2):S5, pp. 1-8, 2010.
Teng et al., "Structural Assessment of the Effects of Amino Acid Substitutions on Protein Stability and Protein-Protein Interaction," Int. J. Comput. Biol. Drug Des., 3(4):334-349, 2010.

* cited by examiner

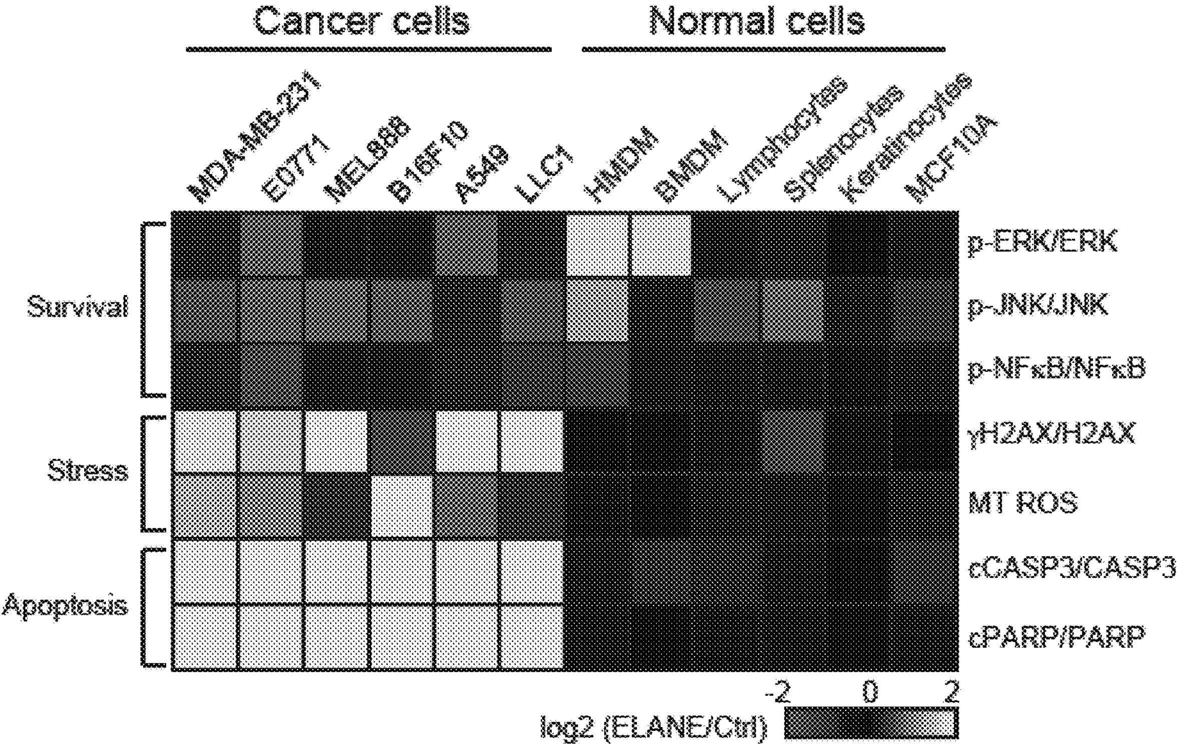
FIG. 1A
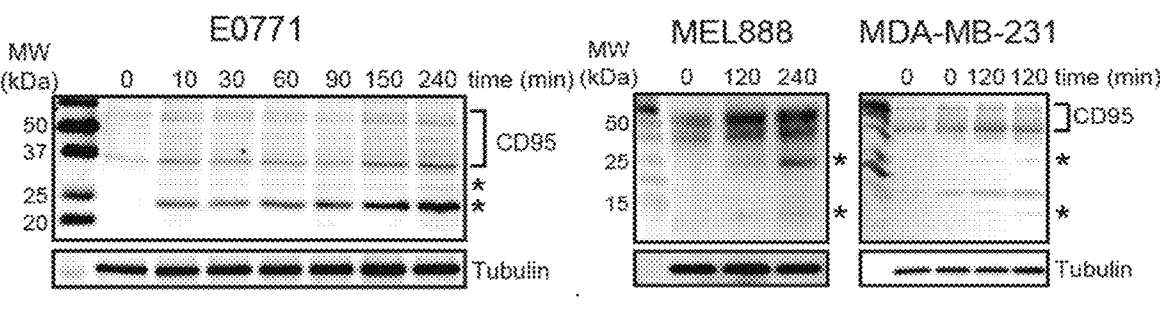
FIG. 1B
FIG. 1C

N-CD95 +
C-CD95 +
kDa
Veh ELANE
37
25
20
15
10

AINLSDVDLSK 2+
DITSDSENSNFRNEI 2+
Band 1
Band 2
Intensity
Retention time (min)
m/z

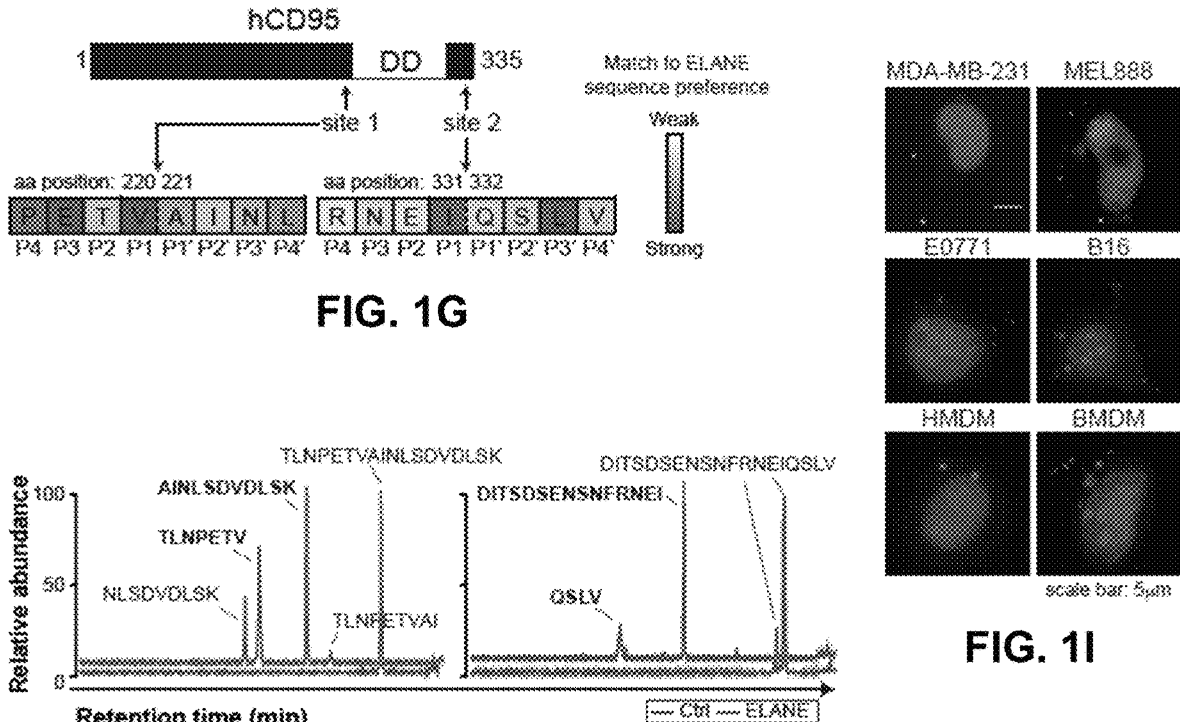
FIG. 1G
FIG. 1H
FIG. 1I
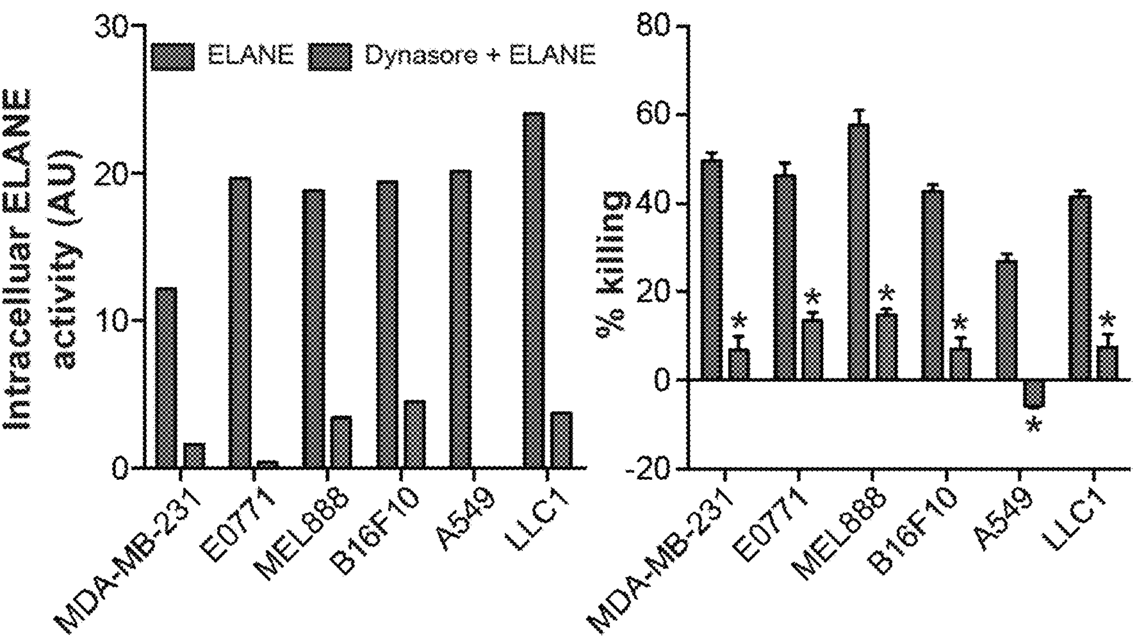
FIG. 1J

Apoptosis quantification

SEQUENCE LISTING

```
<160> NUMBER OF SEQ ID NOS: 5

<210> SEQ ID NO 1
<211> LENGTH: 335
<212> TYPE: PRT
<213> ORGANISM: Homo sapiens

<400> SEQUENCE: 1

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300
```

```
Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335


<210> SEQ ID NO 2
<211> LENGTH: 124
<212> TYPE: PRT
<213> ORGANISM: Artificial Sequence
<220> FEATURE:
<223> OTHER INFORMATION: Synthetic peptide

<400> SEQUENCE: 2

Ser Pro Thr Leu Asn Pro Glu Thr Val Ala Ile Asn Leu Ser Asp Val
1               5                   10                  15

Asp Leu Ser Lys Tyr Ile Thr Thr Ile Ala Gly Val Met Thr Leu Ser
            20                  25                  30

Gln Val Lys Gly Phe Val Arg Lys Asn Gly Val Asn Glu Ala Lys Ile
        35                  40                  45

Asp Glu Ile Lys Asn Asp Asn Val Gln Asp Thr Ala Glu Gln Lys Val
    50                  55                  60

Gln Leu Leu Arg Asn Trp His Gln Leu His Gly Lys Lys Glu Ala Tyr
65                  70                  75                  80

Asp Thr Leu Ile Lys Asp Leu Lys Lys Ala Asn Leu Cys Thr Leu Ala
                85                  90                  95

Glu Lys Ile Gln Thr Ile Ile Leu Lys Asp Ile Thr Ser Asp Ser Glu
            100                 105                 110

Asn Ser Asn Phe Arg Asn Glu Ile Gln Ser Leu Val
        115                 120


<210> SEQ ID NO 3
<211> LENGTH: 115
<212> TYPE: PRT
<213> ORGANISM: Artificial Sequence
<220> FEATURE:
<223> OTHER INFORMATION: Synthetic peptide

<400> SEQUENCE: 3

Ala Ile Asn Leu Ser Asp Val Asp Leu Ser Lys Tyr Ile Thr Thr Ile
1               5                   10                  15

Ala Gly Val Met Thr Leu Ser Gln Val Lys Gly Phe Val Arg Lys Asn
            20                  25                  30

Gly Val Asn Glu Ala Lys Ile Asp Glu Ile Lys Asn Asp Asn Val Gln
        35                  40                  45

Asp Thr Ala Glu Gln Lys Val Gln Leu Leu Arg Asn Trp His Gln Leu
    50                  55                  60

His Gly Lys Lys Glu Ala Tyr Asp Thr Leu Ile Lys Asp Leu Lys Lys
65                  70                  75                  80

Ala Asn Leu Cys Thr Leu Ala Glu Lys Ile Gln Thr Ile Ile Leu Lys
                85                  90                  95

Asp Ile Thr Ser Asp Ser Glu Asn Ser Asn Phe Arg Asn Glu Ile Gln
            100                 105                 110

Ser Leu Val
        115


<210> SEQ ID NO 4
<211> LENGTH: 120
<212> TYPE: PRT
```

-continued

<213> ORGANISM: Artificial Sequence
<220> FEATURE:
<223> OTHER INFORMATION: Synthetic peptide

<400> SEQUENCE: 4

Ser Pro Thr Leu Asn Pro Glu Thr Val Ala Ile Asn Leu Ser Asp Val
1 5 10 15

Asp Leu Ser Lys Tyr Ile Thr Thr Ile Ala Gly Val Met Thr Leu Ser
20 25 30

Gln Val Lys Gly Phe Val Arg Lys Asn Gly Val Asn Glu Ala Lys Ile
35 40 45

Asp Glu Ile Lys Asn Asp Asn Val Gln Asp Thr Ala Glu Gln Lys Val
50 55 60

Gln Leu Leu Arg Asn Trp His Gln Leu His Gly Lys Lys Glu Ala Tyr
65 70 75 80

Asp Thr Leu Ile Lys Asp Leu Lys Lys Ala Asn Leu Cys Thr Leu Ala
85 90 95

Glu Lys Ile Gln Thr Ile Ile Leu Lys Asp Ile Thr Ser Asp Ser Glu
100 105 110

Asn Ser Asn Phe Arg Asn Glu Ile
115 120

<210> SEQ ID NO 5
<211> LENGTH: 111
<212> TYPE: PRT
<213> ORGANISM: Artificial Sequence
<220> FEATURE:
<223> OTHER INFORMATION: Synthetic peptide

<400> SEQUENCE: 5

Ala Ile Asn Leu Ser Asp Val Asp Leu Ser Lys Tyr Ile Thr Thr Ile
1 5 10 15

Ala Gly Val Met Thr Leu Ser Gln Val Lys Gly Phe Val Arg Lys Asn
20 25 30

Gly Val Asn Glu Ala Lys Ile Asp Glu Ile Lys Asn Asp Asn Val Gln
35 40 45

Asp Thr Ala Glu Gln Lys Val Gln Leu Leu Arg Asn Trp His Gln Leu
50 55 60

His Gly Lys Lys Glu Ala Tyr Asp Thr Leu Ile Lys Asp Leu Lys Lys
65 70 75 80

Ala Asn Leu Cys Thr Leu Ala Glu Lys Ile Gln Thr Ile Ile Leu Lys
85 90 95

Asp Ile Thr Ser Asp Ser Glu Asn Ser Asn Phe Arg Asn Glu Ile
100 105 110

METHODS AND COMPOSITIONS RELATED TO THERAPEUTIC PEPTIDES FOR CANCER THERAPY

CROSS REFERENCE TO RELATED APPLICATIONS

This application is a continuation of International Application No. PCT/US2019/067890, filed Dec. 20, 2019, which claims the benefit of priority of U.S. Provisional Patent Application No. 62/782,690 filed Dec. 20, 2018, which are hereby incorporated by reference in their entireties.

BACKGROUND OF THE INVENTION

I. Field of the Invention

Embodiments of the compositions and methods described herein are directed generally to the fields of molecular biology, medicine, and cancer therapy. In particular, embodiments are directed to cancer therapy and anticancer peptide compositions.

II. Description of Related Art

Cancer is an expansionist disease of mutations, which exhibits a high degree of spatial and temporal genetic heterogeneity (Stratton et al., *Nature,* 2009; Vogelstein et al., *Science,* 2013). In addition to overcoming this heterogeneity, eradicating tumor cells while sparing non-cancer cells remains a formidable task. For these reasons, identifying agents that couple broad efficacy across cancer types while maintaining specificity to limit host toxicity has been challenging.

Broad efficacy and specificity are integral properties of innate immunity. The innate immune system evolved to protect against a wide range of infectious pathogens including bacteria, fungi, and protozoa, whose genetic diversity far exceeds cancer. As key effectors of innate immunity, neutrophils eliminate genetically diverse pathogens, and may therefore be ideally poised to perform a comparable function in cancer. Indeed, human blood polymorphonuclear neutrophils (PMNs) can kill cancer cells (Sagiv, *Cell Rep.,* 2015; Yan et. al., *Oncoimmunology,* 2014), and their therapeutic potential is being explored in clinical trials aimed at delivering them as a cell therapy. Despite the emerging focus on human PMNs, the mechanisms by which they kill cancer cells are incompletely understood.

In contrast to the anti-cancer function of PMNs, many studies have shown that tumor-associated neutrophils (TANs) promote tumorigenesis. This conflict could be due to the source and activation status of neutrophils, which can produce striking functional differences (Coffelt et al., *Nat Rev Cancer,* 2016; Eruslanov et al., *Trends Cancer,* 2017; Kruger et al., *PLoS Pathog.,* 2015). For instance, murine studies suggest that tumor cells hijack neutrophils to release molecules to facilitate metastatic spread (Coffelt et al., *Nature,* 2015; Finisguerra et al., *Nature,* 2015). Moreover, increased TAN accumulation is a poor prognostic marker in many cancer types (Coffelt et al., *Nat Rev Cancer,* 2016; Shen et al., *PLoS One,* 2014; Powell et al., *Immunol.,* 2016).

There remains a need for additional anti-cancer compositions and additional therapies for treating cancer having broad anti-cancer efficacy and limited patient toxicity.

SUMMARY OF THE INVENTION

Embodiments of the current invention provide a solution to the problems associated with balancing patient toxicity with broad efficacy of cancer therapy. In particular, embodiments are directed to anti-cancer peptides that demonstrate a broad anti-cancer efficacy with a limited toxicity to normal or non-cancer cells.

Given that human PMNs release extracellular factors that kill a wide range of pathogens, the inventors sought to explore whether these factors have a similar capability to kill cancer cells. Using this strategy, ELANE was identified as the major anti-cancer protein released by human PMNs having a mechanism of action that involves cleaving human CD95 (hCD95) at $V^{220}/A^{221}$ and $I^{331}/Q^{332}$ to liberate a death domain (DD)-containing proteolytic fragment that selectively kills cancer cells. ELANE is shown to have a broad anti-cancer efficacy and selectivity in multiple models.

ELANE has several intriguing properties in pre-clinical models. First, its ability to kill a wide range of cancer cells may enable its implementation without knowledge of their genetics. Second, its specificity to cancer versus non-cancer cells may limit potential toxicity. Third, initial studies suggest that it is challenging for cancer cells to acquire resistance to ELANE. Mechanistically, it is proposed that these properties stem from ELANE's ability to target CD95. Indeed, the killing program, broad efficacy, specificity, and resistance profiles of ELANE closely mimicked those reported in cancer cells treated with shRNA to lower CD95 levels (L. Chen et al., *Nature,* 2010), with one important difference. The proposed mechanism involves a gain-of-function for CD95 (i.e., releasing the DD containing fragment) and not a loss-of-function (i.e., CD95 knockdown). CD95 is known to exert both pro- and anti-apoptotic effects depending on physiological context (Martin-Villalba, Liorens-Bobadilla, Wollny. *Trends Mol Med,* 2013), and studies identify ELANE as a potential therapeutic that capitalizes on its pro-apoptotic function.

The inventors' studies show that ELANE proteolytically liberates the CD95 DD to selectively kill a wide range of cancer cells. Indeed, transiently over-expressing full length CD95 (aa 1-335) or a C-terminal CD95 peptide containing both cleavage sites (aa. 212-335) accelerated ELANE-mediated killing in human cancer cells, while transiently over-expressing the N-terminal domain (aa 1-209) had no effect. However, transiently over-expressing these hCD95 proteins/peptides were insufficient to kill cancer cells in the absence of ELANE. Inducing apoptosis in the absence of ELANE required expressing C-terminal hCD95 peptides that mimicked ELANE cleavage at one or both sites (site 1: aa 221-335; site 2: aa 212-331; both sites: aa 221-331). Demonstration that these hCD95 peptides kill many types of human cancer cells without damaging non-cancer cells supports the approach of delivering specific CD95 peptides or DNA encoding CD95 peptides for the treatment of many cancers.

The data show that some of the human CD95 peptides (which contain ELANE cleavage sites) are not toxic to cancer cells and only make ELANE more efficacious. On the other hand, transiently expressing human CD95 peptides that mimic ELANE cleavage at one or both sites kill cancer cells in the absence of ELANE. C peptide is not toxic, but Cl (mimics cleavage at site 1), C2 (mimics cleavage at site 2), and C1-2 (mimics cleavage at both sites) are all toxic. Also, an N-terminal domain peptide of CD95 and full-length CD95 not toxic to cancer cells. Finally, results showed that expressing the C1-2 peptide in MDA-MB-231 cells induced the same killing mechanism as treating these cells with ELANE (i.e., suppression of survival pathways, and induction of DNA damage, mitochondrial ROS, and apoptosis effectors).

To investigate if expressing the CD95 C1-2 peptide could attenuate tumor growth in vivo, the investigators created MDA-MB-231 cancer cells (TNBC) stably expressing the CD95 C or C1-2 peptide under control of a doxycycline-inducible promoter. In in vitro studies, treatment with doxycycline induced expression of both proteins. Consistent with the transient expression system, cells induced to express the C1-2 peptide underwent apoptosis, while those induced to express the C peptide did not. Moreover, doxycycline-induced expression of the C1-2 peptide in MCF10a cells (non-cancer) failed to induce apoptosis. Analysis of different C1-2 peptide-expressing colonies of MDA-MB-231 cells revealed that the extent of apoptosis was significantly and positively correlated to expression levels of C1-2. MDA-MB-231 cells expressing the doxycycline-inducible C1-2 peptide were injected into mammary fat of mice and tumors were allowed to grow until ~100mm$^3$ in size. At this time, doxycycline was administered to the mice via IP injection or through the food. Results showed that inducing C1-2 expression in MDA-MB-231 cells lessened tumor growth and increased the number of CD45$^+$ immune cells in tumors.

Certain embodiments are directed to a therapeutic or anti-cancer composition including various combinations of anti-cancer peptides or variants thereof, expression vector (s), or expression cassette(s) encoding the same. In certain aspects a peptide composition can include one or more peptide comprising, consisting essentially of, or consisting of the amino acid sequence SPTLNPETVAINLSDVDLSKYITTIAGVMTLSQVKGFVRKNGVNEAKIDEIKNDNVQD TAEQKVQLLRNWHQLHGKKEAYDTLIKDLKKANLCTLAEKIQTIILKDITSDSENSNF RNEIQSLV (SEQ ID NO:2), or segments AINLSDVDLSKYITTIAGVMTLSQVKGFVRKNGVNEAKIDEIKNDNVQDTAEQKVQL LRNWHQLHGKKEAYDTLIKDLKKANLCTLAEKIQTIILKDITSDSENSNFRNEIQSLV (SEQ ID NO:3), and/or SPTLNPETVAINLSDVDLSKYITTIAGVMTLSQVKGFVRKNGVNEAKIDEIKNDNVQD TAEQKVQLLRNWHQLHGKKEAYDTLIKDLKKANLCTLAEKIQTIILKDITSDSENSNF RNEI (SEQ ID NO:4) and/or AINLSDVDLSKYITTIAGVMTLSQVKGFVRKNGVNEAKIDEIKNDNVQDTAEQKVQL LRNWHQLHGKKEAYDTLIKDLKKANLCTLAEKIQTIILKDITSDSENSNFRNEI (SEQ ID NO:5). Certain embodiments are directed to one or more peptide or variant thereof having an amino acid sequence that is 90, 92, 94, 96, 98, 99, to 100% identical, including all values and ranges there between, over 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 124 contiguous amino acids, including all values and ranges there between, of SEQ ID NO:2. A functional segment of the anticancer peptide can start at amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, or 119 and ending at 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 124 of SEQ ID NO:2. In certain aspects an anti-cancer peptide described herein can be modified by chemical modification of amino acid side chains (e.g., crosslinking, glycosylation, etc.) or by including heterologous peptide sequences at the amino or carboxy terminus of the peptide.

The anticancer peptides can be present in a composition, individually, at a concentration of 1, 50, 100, 150, 200, 250, 300, 350, 400, 450 μg/mL to 500, 550, 600, 650, 700, 750, 800, 850, 900, 950 μg/mL; or 1, 10, 20, 30, 40, 50, 60, 70, 80, 90 mg/mL to 100, 110, 120, 130, 140, 150, 160, 170, 180, 190, 200 mg/mL, including all ranges and values there between.

Certain embodiments are directed to one or more anti-cancer peptide and/or compositions containing the same. In certain aspects, one or more peptide components have 90 to 100% identity to a peptide selected from SEQ ID NO:2, SEQ ID NO:3, SEQ ID NO:4, SEQ ID NO:5 or a functional segment thereof. In certain aspects, a peptide has an amino acid sequence that is at least 90% identical to the amino acid sequence of SEQ ID NO:2, SEQ ID NO:3, or SEQ ID NO:4. The peptide component can be coupled to a substrate. In certain aspects, the substrate is a delivery vehicle. The delivery vehicle can be a nanoparticle (e.g., a liposome).

Certain embodiments are directed to methods for treating cancer comprising administering an effective amount of a therapeutic composition comprising one or more peptide that is 90 to 100% identical to a peptide selected from SEQ ID NO:2, SEQ ID NO:3, SEQ ID NO:4, or a functional segment thereof to a subject having cancer. The therapeutic composition can be administered by injection. In certain aspects, the therapeutic composition is administered intratumorally (e.g., by intratumoral injection). The cancer can be a bladder, blood, bone, bone marrow, brain/nervous system, breast, colorectal, esophageal, gastrointestinal, head, kidney, liver, lung, nasopharynx, neck, ovarian, pancreatic, prostate, skin, stomach, testicular, tongue, or uterine cancer. In certain aspects, a peptide is present at a dose of 0.001 mg/kg and 10 mg/kg body weight, preferably between at least, at most, or about 0.1 and 5 mg/kg body weight, most preferably between 0.5 and 1 mg/kg body weight. In other aspects, the method can include administering a second anticancer therapy. The second anticancer therapy can be a chemotherapy, radiotherapy, immunotherapy (e.g., checkpoint inhibitor), or anti-hormonal therapy.

Certain embodiments are directed to methods for inducing apoptosis in a cancer cell comprising contacting the cancer cell with an effective amount of one or more peptide having 90 to 100% identity to a peptide selected from SEQ ID NO:2, SEQ ID NO:3, SEQ ID NO:4, or a functional segment thereof. The cancer cell can be a bladder, blood, bone, bone marrow, brain/nervous system, breast, colorectal, esophageal, gastrointestinal, head, kidney, liver, lung, nasopharynx, neck, ovarian, pancreatic, prostate, skin, stomach, testicular, tongue, or uterine tumor.

The anticancer peptides described herein were discovered as fragments of human CD95, isoform 1, which has an amino acid sequence of MLGIWTLLPLVLTSVARLSSKSVNAQVTDINSKGLELRKTVTTVETQNLEGLHHDGQ FCHKPCPPGERKARDCTVNGDEPDCVPCQEGKEYTDKAHFSSKCRRCRLCDEGHGL EVEINCTRTQNTKCRCKPNFFCN- STVCEHCDPCTKCEHGIIKECTLTSNTKCKEEGSR SNLGWLCLLLLPIPLIVWVKRKEVQKT- CRKHRKENQGSHESPTLNPETVAINLSDVD LSKYIT- TIAGVMTLSQVKGFVRKNGVNEAKIDEIKNDNVQD- TAEQKVQLLRNWHQL HGKKEAYDTLIKDLKKANLCTLAEKIQTIILKDITSD- SENSNFRNEIQSLV (SEQ ID NO:1, accession number NP_000034.1, which is incorporated herein by references as of the application filing date). Amino acids 1 to 25 are a signal peptide and the mature form comprises amino acids 26 to 335. Certain embodiments are directed to one or more peptide or variant thereof having an amino acid sequence that is 90, 92, 94, 96, 98, 99, to 100% identical, including all values and ranges there between, over 10, 50, 60, 70, 80, 90, 100, 110, 120, 130, 140, 150, 160, 170, 180, 190, 200, 210, 220, 230, 240, 250 or 255 contiguous amino acids, including all values and ranges there between, of SEQ ID NO:1. In certain aspects an anti-cancer peptide described herein can be modified by chemical modification of amino acid side chains (e.g., crosslinking, glycosylation, etc.) or by including heterologous peptide sequences at the amino or carboxy terminus of the peptide. The N terminus as referred to herein is from amino acids 1 to 209 of SEQ ID NO:1) and the C terminus as referred to herein is from amino acids 212 to 335 of (SEQ ID NO:1).

Compositions described herein can kill a wide variety of cancer cells, irrespective of cancer cell genetics. Thus, compositions described herein can treat various types of cancers. In certain aspects the cancer is a bladder, blood, bone (e.g., osteosarcoma), bone marrow (e.g., leukemia), brain/nervous system (e.g., neuroblastoma, glioblastoma), breast, colorectal (e.g., colon carcinoma), esophageal, gastrointestinal, head, kidney, liver (e.g., hepatocellular carcinoma), lung (e.g., non-small cell lung cancer), nasopharynx, neck, ovarian, pancreatic, prostate, skin (e.g., melanoma), stomach, testicular, tongue, or uterine cancer. Compositions described herein are toxic to cancer cells, but are not toxic or have a limited toxicity to non-cancer cells.

Certain embodiments are directed to methods for killing a cancer cell by contacting the cancer cell or tumor with an effective amount of a therapeutic anti-cancer peptide composition. In certain aspects the anti-cancer peptide composition is administered to a patient that has cancer. In certain aspects the cancer is a bladder, blood, bone, bone marrow, brain, breast, colorectal, esophageal, gastrointestinal, head, kidney, liver, lung, nasopharynx, neck, ovarian, pancreatic, prostate, skin, stomach, testicular, tongue, or uterine cancer. In certain aspects the anti-cancer peptide composition can further comprise or be administered in conjunction with additional anti-cancer agents to enhance the effectiveness of the peptide composition. In certain aspects, these additional anti-cancer agents can be administered before; during; after; before and during; before and after; during and after; or before, during and after administration of the polypeptide composition. In certain aspects, a composition described herein can be administered before; during; after; before and during; before and after; during and after; or before, during and after administration of an immunotherapy, a chemotherapy, an anti-hormone therapy, or a radiotherapy. In certain aspects, a peptide composition described herein is administered in combination with a chemotherapy, e.g., doxorubicin and/or paclitaxel.

Certain embodiments are directed to an expression vector or expression cassette encoding one or more anti-cancer peptides. A subject can be administered such a vector or cassette for the purpose of expressing one or more anti-cancer peptide in or in proximity to a target cancer or tumor.

The term "effective amount" means an amount effective, at dosages and for periods of time necessary, to achieve the desired therapeutic or prophylactic result.

An "effective amount" of an anti-cancer agent (e.g., peptide composition described herein) in reference to decreasing cancer cell growth, means an amount capable of decreasing, to some extent, the growth of some cancer or tumor cells. The term includes an amount capable of invoking a growth inhibitory, cytostatic and/or cytotoxic effect and/or apoptosis of the cancer or tumor cells.

A "therapeutically effective amount" in reference to the treatment of cancer, means an amount capable of invoking one or more of the following effects: (1) inhibition, to some extent, of cancer or tumor growth, including slowing down growth or complete growth arrest; (2) reduction in the number of cancer or tumor cells; (3) reduction in tumor size; (4) inhibition (i.e., reduction, slowing down, or complete stopping) of cancer or tumor cell infiltration into peripheral organs; (5) inhibition (i.e., reduction, slowing down, or complete stopping) of metastasis; (6) enhancement of anti-tumor immune response, which may, but is not required to, result in the regression or rejection of the tumor, or (7) relief, to some extent, of one or more symptoms associated with the cancer or tumor. The therapeutically effective amount may vary according to factors such as the disease state, age, sex and weight of the individual and the ability of one or more anti-cancer agents to elicit a desired response in the individual. A "therapeutically effective amount" is also one in which any toxic or detrimental effects are outweighed by the therapeutically beneficial effects.

The phrases "treating cancer" and "treatment of cancer" mean to decrease, reduce, or inhibit the replication of cancer cells; decrease, reduce or inhibit the spread (formation of metastases) of cancer; decrease tumor size; decrease the number of tumors (i.e., reduce tumor burden); lessen or reduce the number of cancerous cells in the body; prevent recurrence of cancer after surgical removal or other anti-cancer therapies; or ameliorate or alleviate the symptoms of the disease caused by the cancer.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

The term "expression cassette" refers to a nucleotide sequence that contains at least one coding sequence along with sequence elements that direct the initiation and termination of transcription. An expression cassette may include additional sequences, including, but not limited to promoters, enhancers, and sequences involved in post-transcriptional or post-translational processes.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "consisting of" or "consisting essentially of" may be substituted for the term "comprising" in any embodiment discussed herein.

It is contemplated that any embodiment discussed herein can be implemented with respect to any method or composition, and vice versa. Furthermore, compositions and kits can be used to achieve methods.

Other embodiments are discussed throughout this application. Any embodiment discussed with respect to one aspect applies to other aspects as well and vice versa. The embodiments in the Example section are understood to be embodiments that are applicable to all aspects. Additional objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIGS. 1A-1K. ELANE cleaves CD95 to selectively kill cancer cells. (A): Heatmap summary of ELANE's effects on survival, stress, and apoptosis pathways in cancer cells and healthy cells. See FIG. 2 for quantification. (B-C): Cancer cells were treated with ELANE (100 nM) and CD95 cleavage was assessed by western blotting using anti-N-terminal (B) or anti-C-terminal antibodies (C). *, lower molecular weight CD95 fragment. (D): Cancer cells or non-cancer cells were transduced to overexpress CD95 proteins, and effects on ELANE-mediated apoptosis were quantified by ANXAS at 30 min. n=2/group. See FIG. 1I for transduction and CD95 over-expression. (E): Cleavage of recombinant human CD95 N-terminal (aa 1-173) or C-terminal (aa 212-335) proteins by ELANE was assessed by SDS-PAGE and Coomassie blue staining. (F): Bands from (E) were digested with trypsin and analyzed by mass spectrometry to identify putative ELANE cleavage sites (i.e., peptides with non-tryptic ends). Major non-tryptic peptides were quantified by ion chromatograms. (G): Schematic of ELANE cleavage sites in CD95. Heatmap shows the overlap between the 2 CD95 cleavage sites and ELANE's sequence specificity (at URL web.expasy.org). (H): Cleavage of recombinant peptides corresponding to aa 214-231 and aa 317-335 in CD95 by ELANE was monitored by mass spectrometry. (I): Cancer cells or non-cancer cells were treated with fluorescein-labeled ELANE for 10 min and uptake was visualized by immunofluorescence. (J): ELANE catalytic activity in cancer cell lysates following exposure to ELANE for 30 mins in the presence and absence of Dynasore (60 μM endocytosis inhibitor). Effect of Dynasore on cancer cell killing capability of ELANE (measured by calcein-AM). n=6/group. (K): Cancer cells or non-cancer cells were transduced to overexpress various CD95 proteins, and cell viability in the absence of ELANE was determined by calcein-AM. n=10/group. *, $p<0.05$ Student's t-test.

DETAILED DESCRIPTION OF THE INVENTION

Figures 1D, 1E, 1F:
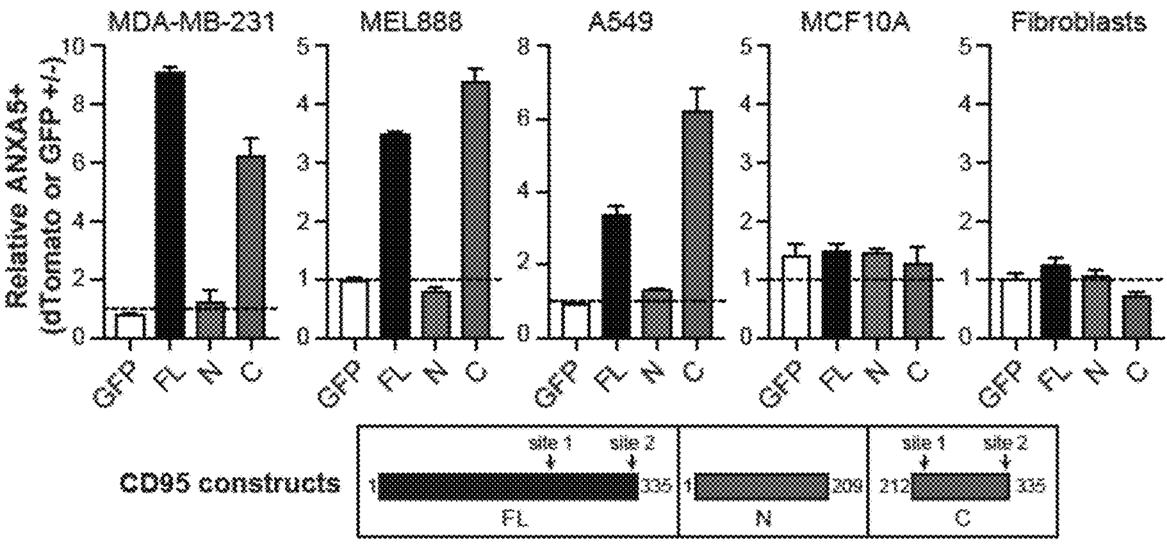

ELANE cleaves CD95 to release proteolytic fragments that selectively kill a wide range of cancer cells. These results, combined with previous work (Chen et al., *Nature,* 2010; Hadji et al., *Cell Rep.,* 2014; Peter et al., *Cell Death Differ.,* 2015), underscore the critical and selective importance of CD95 to cancer cell viability. From a therapeutic perspective, delivering CD95 fragments to the tumor may overcome protective mechanisms and kill cancer cells through a genotype-independent mechanism with a wide therapeutic window. CD95 degradation (production of CD95 fragments) has been identified as the mechanism of action by which ELANE kills cancer cells, and further shows that a broad range of proteases can mimic ELANE's CD95 degradation and cancer cell killing properties. Aspects of the invention are based partially on the following observations. Treating ELANE or neutrophil conditioned media with alpha-1-antitrypsin or PMSF, two irreversible non-competitive ELANE inhibitors, protects cancer cells from apoptosis. ELANE degrades the C-terminal domain of purified CD95. Importantly, this cleavage pattern was distinct from that produced by MMPI, which was previously shown to cleave the extracellular N-terminal domain of CD95, resulting in protection of cancer cells from FASL-mediated apoptosis (Strand et al., *Oncogene,* 2004).

Certain embodiments are directed to a therapeutic or anti-cancer composition including various combinations of anti-cancer peptides or variants thereof, expression vector (s), or expression cassette(s) encoding the same. In certain aspects a peptide composition can include one or more peptide comprising, consisting essentially of, or consisting of the amino acid sequence SPTLNPETVAINLSDVDL-SKYITTIAGVMTLSQVKGFVRKNGVNEAKI-DEIKNDNVQD TAEQKVQLLRNWHQLHGKKEAYDT-LIKDLKKANLCTLAEKIQTIILKDITSDSENSNF RNEIQSLV (SEQ ID NO:2), or segments AINLSDVDL-SKYITTIAGVMTLSQVKGFVRKNGVNEAKI-DEIKNDNVQDTAEQKVQL LRNWHQLHGKKEAYDT-LIKDLKKANLCTLAEKIQTIILKDITSDSENSNFRNEIQSLV (SEQ ID NO:3), and/or SPTLNPETVAINLSDVDLSKYIT-TIAGVMTLSQVKGFVRKNGVNEAKIDEIKNDNVQD TAEQKVQLLRNWHQLHGKKEAYDTLIKDLK-KANLCTLAEKIQTIILKDITSDSENSNF RNEI (SEQ ID NO:4) and/or AINLSDVDLSKYITTI-AGVMTLSQVKGFVRKNGVNEAKIDEIKNDNVQD-TAEQKVQL LRNWHQLHGKKEAYDTLIKDLK-KANLCTLAEKIQTIILKDITSDSENSNFRNEI (SEQ ID NO:5). Certain embodiments are directed to one or more peptide or variant thereof having an amino acid sequence that is 90, 92, 94, 96, 98, 99, to 100% identical, including all values and ranges there between, over 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 124 contiguous amino acids, including all values and ranges there between, of SEQ ID NO:2. A functional segment of the anti-cancer peptide can start at amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, or 119 and ending at 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 124 of SEQ ID NO:2. In certain aspects an anti-cancer peptide described herein can be modified by chemical modification of amino acid side chains (e.g., crosslinking, glycosylation, etc.) or by including heterologous peptide sequences at the amino or carboxy terminus of the peptide.

I. POLYPEPTIDE COMPOSITION AND FORMULATIONS

In certain embodiments, polypeptides and peptides include polypeptides having an amino acid sequence of SEQ ID NO:2, SEQ ID NO:3, SEQ ID NO:4, and/or SEQ ID NO:5, and functional segments thereof. "Polypeptide" refers to any peptide or protein comprising amino acids joined by peptide bonds or modified peptide bonds. "Polypeptide" can include short chain polypeptides, including peptides, oligopeptides or oligomers, and longer chain polypeptides, including proteins. Polypeptides may contain amino acids other than the 20 gene-encoded amino acids. "Polypeptides" include amino acid sequences modified either by natural processes, such as post-translational processing, or by chemical modification or other synthetic techniques well known in the art. Modifications can occur anywhere in a polypeptide, including the peptide backbone, the amino acid side-chains, and the amino terminus or the carboxy terminus. It will be appreciated that the same type of modification may be present in the same or varying degrees at several sites in a given polypeptide. Also, a given polypeptide may contain many types of modifications. Modifications include terminal fusion (N- and/or C-terminal), acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

There are a wide variety of detectable labels that can be attached to polypeptides and variants thereof. For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCPCy5.5, PE-Cy5, PE-Cy5.5, PE-Cy7, PE-Texas Red, and APC-Cy7. Other fluorophores include, inter alia, Alexa Fluor® 350, Alexa Fluor® 488, Alexa 25 Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7. For secondary detection using labeled avidin, streptavidin, captavidin or neutravidin, the polypeptides can usefully be labeled with biotin. Polypeptides can be labeled with radioisotopes, such as $^{33}$P, $^{32}$P, $^{35}$S, $^{3}$H, and $^{125}$I. As another example, when the polypeptide may be used for targeted radiotherapy, the label can be $^{3}$H, $^{228}$Th, $^{227}$Ac, $^{225}$Ac, $^{223}$Ra, $^{213}$Bi, $^{212}$Pb, $^{212}$Bi, $^{211}$At, $^{203}$Pb, $^{194}$Os, $^{188}$Re, $^{186}$Re, $^{153}$Sm, $^{149}$Tb, $^{131}$I, $^{125}$I, $^{105}$Rh, $^{99}$MTc, $^{97}$Ru, $^{90}$Y, $^{90}$Sr, $^{88}$Y, $^{72}$Se, $^{67}$Cu, or $^{47}$Sc.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated polypeptide refers to one that can be administered to a subject as an isolated polypeptide; in other words, the polypeptide may not simply be considered "isolated" if it is adhered to a column or embedded in a gel. Moreover, an "isolated nucleic acid fragment" or "isolated peptide" is a nucleic acid or protein fragment that is not naturally occurring as a fragment and/or is not typically in the functional state.

The term "amino acid" or "residue" should be understood to mean a compound containing an amino group ($NH_2$), a carboxylic acid group (COOH), and any of various side groups, that have the basic formula $NH_2CHRCOOH$, and that link together by peptide bonds to form proteins. Amino acids may, for example, be acidic, basic, aromatic, polar or derivatized. Non-standard amino acids may be referred to as "non-canonical" amino acids. Amino acids are naturally found in the α- and L-form, however, β- and D-form amino acids can also be prepared.

A one-letter abbreviation system is frequently applied to designate the identities of the twenty "canonical" amino acid residues generally incorporated into naturally occurring peptides and proteins, these designations are well known in the art. Such one-letter abbreviations are entirely interchangeable in meaning with three-letter abbreviations, or non-abbreviated amino acid names. The canonical amino acids and their three letter and one letter codes include Alanine (Ala) A, Glutamine (Gln) Q, Leucine (Leu) L, Serine (Ser) S, Arginine (Arg) R, Glutamic Acid (Glu) E, Lysine (Lys) K, Threonine (Thr) T, Asparagine (Asn) N, Glycine (Gly) G, Methionine (Met) M, Tryptophan (Trp) W, Aspartic Acid (Asp) D, Histidine (His) H, Phenylalanine (Phe) F, Tyrosine (Tyr) Y, Cysteine (Cys) C, Isoleucine (Ile) I, Proline (Pro) P, and Valine (Val) V.

Certain embodiments also include variants of the polypeptides described herein. Variants of the disclosed polypeptides may be generated by making amino acid additions or insertions, amino acid deletions, amino acid substitutions, and/or chemical derivatives of amino acid residues within the polypeptide sequence. Desired amino acid substitutions (whether conservative or non-conservative) can be determined by those skilled in the art in accordance with guidance provided herein for increasing stability, while maintaining or enhancing potency of the polypeptides. In certain embodiments, conservative amino acid substitutions can encompass non-naturally occurring amino acid residues which are typically incorporated by chemical peptide synthesis rather than by synthesis in biological systems.

Conservative modifications can produce peptides having functional, physical, and chemical characteristics similar to those of the peptide from which such modifications are made. In contrast, substantial modifications in the functional and/or chemical characteristics of peptides may be accomplished by selecting substitutions in the amino acid sequence that differ significantly in their effect on maintaining (a) the structure of the molecular backbone in the region of the substitution, for example, as an α-helical conformation, (b) the charge or hydrophobicity of the molecule at the target site, or (c) the size of the molecule. For example, a "conservative amino acid substitution" may involve a substitution of a native amino acid residue with a non-native residue such that there is little or no effect on the polarity or charge of the amino acid residue at that position.

Recombinant DNA- and/or RNA-mediated protein expression and protein engineering techniques, or any other methods of preparing peptides, are applicable to the making of the polypeptides disclosed herein or expressing the polypeptides disclosed herein in a target cell or tissue. The term "recombinant" should be understood to mean that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well-known molecular biological procedures. Examples of such molecular biological procedures are found in Maniatis et al., *Molecular Cloning. A Laboratory Manual,* Cold Spring Harbor Laboratory, Cold Spring Harbor, N.Y., 1982. A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid.

The polypeptides can be made in transformed host cells according to methods known to those of skill in the art. Briefly, a recombinant DNA molecule, or construct, coding for the peptide is prepared. Methods of preparing such DNA molecules are well known in the art. For instance, sequences encoding the peptides can be excised from DNA using suitable restriction enzymes. Any of a large number of available and well-known host cells may be used in the practice of various embodiments. The selection of a particular host is dependent upon a number of factors, which include, for example, compatibility with the chosen expression vector, toxicity of the polypeptides encoded by the DNA molecule, rate of transformation, ease of recovery of the polypeptides, expression characteristics, bio-safety, and costs. A balance of these factors should be struck with the understanding that not all hosts may be equally effective for the expression of a particular DNA sequence. Within these general guidelines, useful microbial host cells in culture include bacteria (such as *Escherichia coli* sp.), yeast (such as *Saccharomyces* sp.) and other fungal cells, insect cells, plant cells, mammalian (including human) cells, e.g., CHO cells and HEK293 cells. Modifications can be made at the DNA level, as well. The peptide-encoding DNA sequence may be changed to codons more compatible with the chosen host cell. For *E. coli,* optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired polypeptides are expressed. In addition, the DNA optionally further encode, 5' to the coding region of a fusion protein, a signal peptide sequence (e.g., a secretory signal peptide) operably linked to the expressed polypeptide.

The polypeptides can also be made by synthetic methods. Solid phase synthesis can be used as a technique of making individual polypeptides since it is the most cost-effective method of making small peptides. For example, well known solid phase synthesis techniques include the use of protecting groups, linkers, and solid phase supports, as well as specific protection and deprotection reaction conditions, linker cleavage conditions, use of scavengers, and other aspects of solid phase peptide synthesis. Suitable techniques are well known in the art. See, e.g., Merrifield, *Chem. Polypeptides,* Katsoyannis and Panayotis eds., pp. 335-361, 1973; Merrifield, *J. Am. Chem. Soc.* 85: 2149, 1963; Davis et al., *Biochem. Intl.* 10:394-414, 1985; Stewart and Young, *Solid Phase Peptide Synthesis,* 1969; U.S. Pat. 3,941,763; Finn et al., *The Proteins, 3rd ed.,* 2:105-253, 1976; and Erickson et al., *The Proteins, 3rd ed.,* 2: 257-527, 1976; "Protecting Groups in Organic Synthesis," 3rd ed., T. W. Greene and P. G. M. Wuts, Eds., John Wiley & Sons, Inc., 1999; NovaBiochem Catalog, 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; "Protecting Groups," P. J. Kocienski, Ed., Georg Thieme Verlag, Stuttgart, Germany, 1994; "Fmoc Solid Phase Peptide Synthesis, A Practical Approach," W. C. Chan and P. D. White, Eds., Oxford Press, 2000; G. B. Fields et al., Synthetic Peptides: A User's Guide, 77-183, 1990.

A composition that includes a polypeptide covalently linked, attached, or bound, either directly or indirectly through a linker moiety, to another peptide, vehicle (e.g., carrier), or a half-life extending moiety is a "conjugate" or "conjugated" molecule, whether conjugated by chemical means (e.g., post-translationally or post-synthetically) or by recombinant fusion. Conjugation of the polypeptides can be via the N-terminus and/or C-terminus of the polypeptide, or can be intercalary as to the peptide's primary amino acid sequence. Due to the specificity of the polypeptides for cancer cells, the polypeptides can be coupled to other cytotoxic moieties to promote specific delivery to cancer cells and to enhance the cytotoxicity of the polypeptides described herein. A linker can be used to create fusion protein(s) that allow introduction of additional moieties to enhance killing or localization of a polypeptide. Specific moieties of interest may include chemotherapeutics, pro-apoptotic factors, targeted therapeutics (e.g., kinase inhibitors, etc.), or other agents that promote killing.

In some embodiments, 1, 2, 3, or 4 polypeptides is/are coupled to or encapsulated in the same or different delivery vehicle, such as a carrier (e.g., a particle), or a liposome. In some embodiments, coupling of the polypeptide(s) to the carrier includes one or more covalent and/or non-covalent interactions. In one embodiment the carrier is a metallic or polymeric particle. In one embodiment, the carrier is a liposome. The particles can be microscopic or nanoscopic in size. In certain aspects a particle has a diameter of from at least, at most, or about 0.1 μm to at least, at most, or about 10 μm. In another aspect, the particle has an average diameter of at least, at most, or about 0.3 μm to at least, at most, or about 5 μm, 0.5 μm to at least, at most, or about 3 μm, or 0.2 μm to at least, at most, or about 2 μm. In certain aspects the particle can have an average diameter of at least, at most, or about 0.1 μm, or at least, at most, or about 0.2 μm or at least, at most, or about 0.3 μm or at least, at most, or about 0.4 μm or at least, at most, or about 0.5 μm or at least, at most, or about 1.0 μm or at least, at most, or about 1.5 μm or at least, at most, or about 2.0 μm or at least, at most, or about 2.5 μm or at least, at most, or about 3.0 μm or at least, at most, or about 3.5 μm or at least, at most, or about 4.0 μm or at least, at most, or about 4.5 μm or at least, at most, or about 5.0 μm, including all values and ranges there between.

In some embodiments, the charge of a carrier (e.g., positive, negative, neutral) is selected to impart application-specific benefits (e.g., physiological compatibility, beneficial surface-peptide interactions, etc.). In some embodiments, a carrier has a net neutral or negative charge (e.g., to reduce non-specific binding to cell surfaces which, in general, bear a net negative charge). In some instances, a carrier is coupled to multiple polypeptides and can have 2, 3, 4, 5, 6, 7, 8, 9, 10 . . . 20 . . . 50 . . . 100, or more copies of a certain polypeptide or combinations of polypeptides exposed on the surface. In some embodiments, a carrier displays a single type of polypeptide. In some embodiments, a carrier displays multiple different polypeptides on the surface.

The terms "packaged", "encapsulation" and "entrapped," as used herein, refer to the incorporation or association of a polypeptide in or with a liposome or similar vehicle. The polypeptide may be associated with the lipid bilayer or present in the aqueous interior of the liposome, or both.

The liposomes can be formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream. Various types of lipids are used to produce liposomes. For example, amphipathic lipids that find use are zwitterionic, acidic, or cationic lipids. Examples of zwitterionic amphipathic lipids are phosphatidylcholines, phosphatidylethanolamines, sphingomyelins, etc. Examples of acidic amphipathic lipids are phosphatidylglycerols, phosphatidylserines, phosphatidylinositols, phosphatidic acids, etc. Examples of cationic amphipathic lipids are diacyl trimethylammonium propanes, diacyl dimethylammonium propanes, stearylamine, etc. Examples of neutral lipids include diglycerides, such as diolein, dipalmitolein, and mixed caprylin-caprin; triglycerides, such as triolein, tripalmitolein, trilinolein, tricaprylin, and trilaurin;

and combinations thereof. Additionally, cholesterol or plant sterols are used in some embodiments, e.g., to make multivesicular liposomes.

A variety of methods are available for preparing liposomes as described in, e.g., Szoka et al., *Ann. Rev. Biophys. Bioeng.* 9:467 (1980), U.S. Pat. Nos. 4,235,871; 4,501,728; and 4,837,028, all of which are incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. Alternatively, the lipids may be dissolved in a suitable solvent, such as tertiary butanol, and then lyophilized to form a more homogeneous lipid mixture that is in a more easily hydrated powder-like form. This film or powder is covered with an aqueous buffered solution and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

Multilamellar liposomes are formed, e.g., by agitation of the dispersion, preferably through the use of a thin-film evaporator apparatus or through shaking or vortex mixing.

Unilamellar vesicles are formed by the application of a shearing force to an aqueous dispersion of the lipid solid phase, e.g., by sonication or the use of a microfluidizing apparatus such as a homogenizer or a French press. Shearing force can also be applied using injection, freezing and thawing, dialyzing away a detergent solution from lipids, or other known methods used to prepare liposomes. The size of the liposomes can be controlled using a variety of known techniques including controlling the duration of shearing force.

"Unilamellar liposomes," also referred to as "single lamellar vesicles," are spherical vesicles that include one lipid bilayer membrane that defines a single closed aqueous compartment. The bilayer membrane includes two layers (or "leaflets") of lipids; an inner layer and an outer layer. The outer layer of the lipid molecules is oriented with the hydrophilic head portions toward the external aqueous environment and the hydrophobic tails pointed downward toward the interior of the liposome. The inner layer of the lipid lay directly beneath the outer layer with the lipids oriented with the heads facing the aqueous interior of the liposome and the tails oriented toward the tails of the outer layer of lipid.

"Multilamellar liposomes" also referred to as "multilamellar vesicles" or "multiple lamellar vesicles," include more than one lipid bilayer membrane, which membranes define more than one closed aqueous compartment. The membranes are concentrically arranged so that the different membranes are separated by aqueous compartments, much like an onion.

II. PHARMACEUTICAL FORMULATIONS AND ADMINISTRATION

Embodiments are related to compositions including 1, 2, 3, 4, or more anti-cancer peptides, or variants or functional segments thereof with one or more of the following: a pharmaceutically acceptable diluent; a carrier; a solubilizer; an emulsifier; and/or a preservative. Such compositions may contain an effective amount of at least one anti-cancer agent or complex. Thus, the use of one or more anti-cancer agents described herein in the preparation of a pharmaceutical composition of a medicament is also included. Such compositions can be used in the treatment of a variety of cancers.

The anti-cancer agents may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the anti-cancer agents that are provided, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18 th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from at least, at most, or about 4.0 to at least, at most, or about 8.5, or alternatively, between at least, at most, or about 5.0 to 8.0, including all values and ranges there between. Pharmaceutical compositions can comprise TRIS buffer of at least, at most, or about pH 6.5-8.5, including all values and ranges there between, or acetate buffer of at least, at most, or about pH 4.0-5.5, including all values and ranges there between, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. Local administration to a tumor (e.g., intratumorally) in question is also contemplated. When administering the compositions by injection, the administration may be by continuous infusion or by single or multiple boluses. For parenteral administration, the anti-metastatic agents may be administered in a pyrogen-free, parenterally acceptable aqueous solution comprising the desired anti-cancer agents in a pharmaceutically acceptable vehicle. A particularly suitable vehicle for parenteral injection is sterile distilled water in which one or more anti-cancer agents are formulated as a sterile, isotonic solution, properly preserved.

Once the pharmaceutical compositions have been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, at least, at most, or about 0.1% to at least, at most, or about 0.5% (w/v). Surfactant stabilizers, such as TWEEN®-20 or TWEEN®-80 (ICI Americas, Inc., Bridgewater, N.J., USA), may also be added in conventional amounts.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents. Compositions for parental administration are also sterile, substantially isotonic and made under GMP conditions.

For the compounds described herein, alone or as part of a pharmaceutical composition, such doses are between at least, at most, or about 0.001 mg/kg and 10 mg/kg body weight, preferably between at least, at most, or about 1 and 5 mg/kg body weight, most preferably between 0.5 and 1 mg/kg body weight, including all values and ranges there between.

Therapeutically effective doses will be easily determined by one of skill in the art and will depend on the severity and course of the disease, the patient's health and response to treatment, the patient's age, weight, height, sex, previous medical history and the judgment of the treating physician.

In some methods, the cancer cell is a tumor cell. The cancer cell may be in a patient. The patient may have a solid tumor. In such cases, embodiments may further involve performing surgery on the patient, such as by resecting all or part of the tumor. Compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

The method may further comprise administering to subject a second cancer therapy selected from chemotherapy, radiotherapy, immunotherapy, hormonal therapy, or gene therapy. The method may further comprise administering 1, 2, 3, 4, or all 5 polypeptides or variants thereof to the subject more than once. In certain aspects, a second cancer therapy can be the administration of an ELANE, or similar protease in combination with the anti-cancer peptides described herein.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. Moreover, a cell or a patient may be administered a microtubule stabilizing agent, including, but not limited to, taxane, as part of methods. It is specifically contemplated that any of the compounds or derivatives or analogs, can be used with these combination therapies.

In certain aspects, other therapeutic agents useful for combination cancer therapy with the polypeptides described herein include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the inhibitors can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Immunotherapy or biological response modifier therapy can be used in combination with the therapies described herein. These treatments use the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), viral vaccines, dendritic cell vaccines, antigen vaccines, anti-idiotype vaccines, DNA vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin).

In certain embodiments passive immunotherapies, such as, naked monoclonal antibody drugs can be used in combination with the polypeptide compositions described herein to treat cancer. Examples of these naked monoclonal antibody drugs include, but are not limited to Rituximab (Rittman), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irinotecan to treat, for example, advanced colorectal cancer and head and neck cancers; and Bevacizumab (Avastin) which is an anti-angiogenesis therapy that works against the VEGF protein and is used, for example, in combination with chemotherapy to treat, for example, metastatic colorectal cancer. Further examples of therapeutic antibodies that can be used include, but are not limited to, HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-$\alpha V\beta 3$ integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (DEC Pharm/Genentech, Roche/Zettyaku); LYIMPHOCIDE™ which is a humanized anti-CD22 IgG antibody (Immunomedics); LYIMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (DEC Pharm/Mitsubishi); ZEVALIN™ is a radiolabeled murine anti-CD20 antibody (IDEC/Schering AG); IDEC-131 is a humanized anti-CD40L antibody (IDEC/Eisai); IDEC-151 is a primatized anti-CD4 antibody (DEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Mexion Pharm); D2E7 is a humanized anti-TNF-a antibody (CAT/BASF); CDP870 is a humanized anti-TNF-$\alpha$ Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-$\alpha$ IgG4 antibody (Celltech); LDP-02 is a humanized anti-$\alpha 4\beta 7$ antibody (LeukoSite/Genentech); Orthodone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-$\beta 2$ antibody (Cambridge Ab Tech).

In certain embodiments passive immunotherapies, such as, conjugated monoclonal antibodies can be used in combination with the polypeptide compositions described herein to treat cancer. Examples of these conjugated monoclonal antibodies include, but are not limited to radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

In certain embodiments targeted therapies containing toxins can be used in combination with the polypeptide compositions described herein to treat cancer. Targeted therapies containing toxins are toxins linked to growth factors, or in particular embodiments the polypeptides described herein, and do not contain antibodies Some embodiments also include the use of adjuvant immunotherapies in combination with the polypeptide compositions described herein, such adjuvant immunotherapies include, but are not limited to, cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of, interleukins, for example, IL-2 with other cytokines, such as IFN-alpha.

Some embodiments also include the use of hormonal therapies (anti-hormonal agents) in combination with the polypeptide compositions described herein. Anti-hormonal agents include, but are not limited to agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® Ril-2; LURTOTECAN® topoisomerase 1 inhibitor; ABARELIX® rmRH; and pharmaceutically acceptable salts, acids or derivatives of any of the above.

In some embodiments, the cancer that is administered the composition(s) described herein may be a bladder, blood, bone, bone marrow, brain, breast, colorectal, esophagus, gastrointestine, head, kidney, liver, lung, nasopharynx, neck, ovary, pancreas, prostate, skin, stomach, testicular, tongue, or uterus cell.

III. EXPRESSION AND EXPRESSION VECTORS

The nucleic acids encoding any polypeptide(s) (e.g., anti-cancer peptides) described herein can be inserted into or employed with any suitable expression system. Recombinant expression can be accomplished using a vector, such as a plasmid, virus, etc. The vector can include a promoter operably linked to nucleic acid encoding one or more polypeptides. The vector can also include other elements required for transcription and translation. As used herein, vector refers to any carrier containing exogenous DNA. Thus, vectors are agents that transport the exogenous nucleic acid into a cell without degradation and include a promoter yielding expression of the nucleic acid in the cells into which it is delivered. Vectors include but are not limited to plasmids, viral nucleic acids, viruses, phage nucleic acids, phages, cosmids, and artificial chromosomes. A variety of prokaryotic and eukaryotic expression vectors suitable for carrying, encoding and/or expressing nucleic acids encoding proteases can be produced. Such expression vectors include, for example, pET, pET3d, pCR2.1, pBAD, pUC, and yeast vectors. The vectors can be used, for example, in a variety of in vivo and in vitro situations. The vector may be a gene therapy vector, for example an adenovirus vector, a lentivirus vector or a CRISP-R vector.

The expression cassette, expression vector, and sequences in the cassette or vector can be heterologous. As used herein, the term "heterologous" when used in reference to an expression cassette, expression vector, regulatory sequence, promoter, or nucleic acid refers to an expression cassette, expression vector, regulatory sequence, or nucleic acid that has been manipulated in some way. For example, a heterologous promoter can be a promoter that is not naturally linked to a nucleic acid to be expressed, or that has been introduced into cells by cell transformation procedures. A heterologous nucleic acid or promoter also includes a nucleic acid or promoter that is native to an organism but that has been altered in some way (e.g., placed in a different chromosomal location, mutated, added in multiple copies, linked to a non-native promoter or enhancer sequence, etc.). Heterologous nucleic acids may comprise sequences that comprise cDNA. Heterologous coding regions can be distinguished from endogenous coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that are linked to a coding region to which they are not linked in nature.

Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors. Retroviral vectors that can be employed include those described in by Verma, I. M., Retroviral vectors for gene transfer. In Microbiology-1985, American Society for Microbiology, pp. 229-232, Washington, (1985). For example, such retroviral vectors can include Murine Maloney Leukemia virus, MMLV, and other retroviruses that express desirable properties. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid.

A variety of regulatory elements can be included in the expression cassettes and/or expression vectors, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleic acid segment encoding a protease. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 nucleotides in length, and they function in cis. Enhancers function to increase transcription from nearby promoters. Enhancers, like promoters, also often contain response elements that mediate the regulation of transcription. Enhancers often determine the regulation of expression.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the expression constructs.

The expression of one or more protease from an expression cassette or expression vector can be controlled by any promoter capable of expression in prokaryotic cells or eukaryotic cells. Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. Vectors for bacterial expression include pGEX-5X-3, and for eukaryotic expression include pClneo-CMV.

The expression cassette or vector can include nucleic acid sequence encoding a marker product. This marker product is used to determine if the gene has been delivered to the cell and once delivered is being expressed. Preferred marker genes are the *E. coli* lacZ gene which encodes β-galactosidase and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)).

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes or viruses. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. *Cancer Res.* 53:83-88, (1993)). Appropriate means for transfection, including viral vectors, chemical transfectants, or physico-mechanical methods such as electroporation and direct diffusion of DNA, are described by, for example, Wolff et al., *Science,* 247, 1465-1468, (1990); and Wolff, Nature, 352, 815-818, (1991).

For example, the nucleic acid molecule, expression cassette and/or vector encoding a protease can be introduced to a cell by any method including, but not limited to, calcium-mediated transformation, electroporation, microinjection, lipofection, particle bombardment and the like. The cells can be expanded in culture and then administered to a subject, e.g., a mammal such as a human. The amount or number of cells administered can vary but amounts in the range of about $10^6$ to about $10^9$ cells can be used. The cells are generally delivered in a physiological solution such as saline or buffered saline. The cells can also be delivered in a vehicle such as a population of liposomes, exosomes or microvesicles.

The protease can be produced by a transgenic cell that produces exosomes or microvesicles that contain the protease. Exosomes and microvesicles mediate the secretion of a wide variety of proteins, lipids, mRNAs, and micro RNAs, interact with neighboring cells, and can thereby transmit signals, proteins, lipids, and nucleic acids from cell to cell (see, e.g., Shen et al., *J Biol Chem.* 286(16): 14383-14395 (2011); Hu et al., *Frontiers in Genetics* 3 (April 2012); Pegtel et al., *Proc. Nat'l Acad Sci* 107(14): 6328-6333 (2010); WO/2013/084000; each of which is incorporated herein by reference in its entirety.

Thus, transgenic cells with a heterologous expression cassette or expression vector that expresses one or more protease can be administered to a subject and the exosomes produced by the transgenic cells deliver the protease to a tumor and/or cancer cells in the subject.

In accordance with the above, the present disclosure relates to methods to derive vectors, particularly plasmids, cosmids, viruses and bacteriophages used conventionally in genetic engineering and in gene therapy that comprise a nucleic acid molecule encoding the polypeptide sequence of a protease defined herein. In certain cases, the vector is an expression vector and/or a gene transfer or targeting vector. Expression vectors derived from viruses such as retroviruses, vaccinia virus, adeno-associated virus, herpes viruses, or bovine papilloma virus, may be used for delivery of the recited polynucleotides or vector into targeted cell populations. Methods that are well known to those skilled in the art can be used to construct recombinant vectors. Alternatively, the recited nucleic acid molecules and vectors can be reconstituted into liposomes for delivery to target cells. The vectors containing the nucleic acid molecules of the disclosure can be transferred into the host cell by well-known methods, which vary depending on the type of cellular host.

Another aspect of the invention is directed to a gene therapy vector comprising anti-cancer peptide construct. Gene therapy vectors are known in the art and include, but are not limited to, lentiviral vectors, adenoviral vectors, adeno-associated viral vectors, plasmids and the like. Construction of a gene therapy vector of the invention can be done by methods known in the art. In certain aspects a gene therapy vector can be administered in an amount of about, at most, or at least 10, 100, 1000, $1\times10^4$, $1\times10^5$, $1\times10^6$, $1\times10^7$, $1\times10^8$, $1\times10^9$, $1\times10^{10}$, $1\times10^{11}$, $1\times10^{12}$ viral particles (VP) or colony forming units (CFU), including all values and ranges there between.

As an example of a gene therapy vector an expression cassette can be included in a lentiviral vector. The therapeutic vector can be transduced into cells ex vivo and the cells are delivered to the patient. Likewise, a therapeutic vector of the invention can be delivered directly to the patient.

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Neutrophil Elastase Cleaves CD95 to Broadly and Safely Kill Cancer Cells

A. Results

Human neutrophils release factors that selectively kill cancer cells. Human peripheral polymorphonuclear neutrophils (PMNs) have a short half-life in vivo (~8h), and rapidly undergo apoptosis to release factors extracellularly with potent anti-microbial properties (Dancey et al., *J Clin Invest.,* 1976; Nathan et al., *Nat Rev Immunol.,* 2006). To determine if apoptotic neutrophils also release factors that kill cancer cells, 35 different human/murine cancer cells were treated with serum-free media conditioned by purified PMNs cycled to apoptosis (PMN media). PMN media effectively killed all cancer cell lines tested within 24 h. In sharp contrast, PMN media did not kill any of the 6 human/mouse normal or non-cancer cells tested. Conditioned media from omental neutrophils (ONs) isolated from healthy subjects also selectively killed cancer cells. However, murine neutrophils from a variety of sources and activation states lacked this cancer cell killing capability.

The cancer cell killing capability of PMN media was inhibited by culturing cancer cells in fetal bovine, murine, or human serum. However, serum could not rescue cancer cells if delivered following a 5-min exposure to PMN media under serum-free conditions, suggesting that serum contains an inhibitor(s) that directly antagonizes anti-cancer factor(s) in PMN media (see below). The reliance of PMN media killing on serum-free conditions, may explain why previous studies, conducted in the presence of serum, showed that human neutrophils require cell-to-cell contact to kill cancer cells (Yan et al., *Oncoimmunology,* 2014).

To begin to understand mechanisms by which PMN media killed cancer cells, representative studies were focused on three cancer types with different mutational spectra: melanoma (MEL888, B16F10), lung cancer (A549, LLC1), and triple-negative breast cancer (MDA-MB-231, E0771). It was found that PMN media killed all of these cancer cells by inducing apoptosis.

Studies were performed to determine if PMN media could induce cancer cell apoptosis in vivo. Mice were injected with a variety of cancer cells in syngeneic models (E0771, LLC1, B 16F10) and a PDX model of triple-negative breast cancer (TNBC, 4195) to create tumors of ~100 $mm^3$ in size. Because serum antagonized the cancer killing capability of PMN media in vitro, PMN media was delivered intratumorally (IT). Tumors were injected daily with human serum albumin (HSA) or PMN media once/day for 5 days, and apoptosis was examined by TUNEL, cleaved PARP (cPARP), and cleaved CASP3 (cCASP3) staining. PMN media attenuated tumor growth and induced cancer cell apoptosis in every model tested. Effects in syngeneic models were not due to injecting human proteins into immune competent mice, since inactivating the bioactive factor in PMN media blocked its anti-tumor action. In contrast, media from murine bone marrow-derived neutrophils (BMDNs) could not attenuate tumorigenesis in vivo, which agrees with their inability to kill cancer cells in vitro. Consistent with its lack of toxicity to normal or non-cancer cells in vitro, PMN media injected into mammary fat pads of tumor-free C57BL/6 mice (once/day for 5 days) did not induce apoptosis at the injection site, nor did it affect body weight, spleen weight, or liver function.

ELANE is the major anti-cancer protein released by human PMNs. Findings suggest that PMNs release factor(s) that selectively kill a wide range of cancer cells in vitro and in vivo. To identify the factor(s) responsible, a quantitative cancer cell killing assay was developed to track the bioactive factor(s), and used boiling, dialysis, and centricon experiments to justify searching for a protein. Next, studies were performed to purify the protein(s) responsible. PMN media was prepared for fractionation by clarifying it through a 0.22 μm filter. Surprisingly, this step eliminated the cancer killing activity of PMN media from 2 independent donors without lowering total protein levels, suggesting a selective depletion of the bioactive protein(s).

Shotgun proteomics analyses identified 890 proteins (≥2 peptides, FDR<1%) in PMN media, and only 2 of those were significantly lowered (G-test, $p<0.05$ with Bonferroni correction) by filtration in both donors: neutrophil elastase (ELANE) and eosinophil cationic protein (ECP). ELANE is a serine protease which previous studies suggest promotes tumorigenesis (Houghton et al., *Nat Med.,* 2010) while ECP is a pore-forming protein that is toxic to both cancer cells and healthy cells (Young et al., *Nature,* 1986).

Two approaches were used to determine if ELANE and/or ECP were responsible for the selective cancer killing activity of PMN media. First, ELANE or ECP was immune-depleted from PMN media and found that depleting either protein attenuated the ability of PMN media to kill MDA-MB-231 cells. Second, cancer cells or normal or non-cancer cells were treated with purified ELANE or ECP and cell viability was monitored. ELANE killed MDA-MB-231 cells in a dose-dependent manner, and this effect was selective since it did not kill Human monocyte-derived macrophages (HMDMs). In contrast, ECP killed MDA-MB-231 cells only at doses that were also toxic to HMDMs.

Next, MDA-MB-231 cells were treated with concentrations of ELANE (0.25 μg/mL) and ECP (0.05 μg/mL) that were present in PMN media. Although PMN media levels of ECP could not kill these cells alone, they significantly enhanced the selective killing capability of ELANE, suggesting a synergy between these two proteins.

Since ELANE influences biological pathways by proteolysis (Pham, *Nat Rev Immunol.,* 2006) it was hypothesized that its anti-cancer function may require catalytic activity, and that ECP might enhance this activity to support synergistic killing. ELANE was treated with PMSF or alpha-1-anti-trypsin (A1AT), inactivation was confirmed with a chromogenic substrate activity assay, and it was found that catalytically inactive ELANE could no longer kill cancer cells. PMSF or A1AT treatment also eliminated the ability of PMN media to kill cancer cells in vitro and in vivo. These results suggest that ELANE is the major anti-cancer factor in PMN media. Indeed, ELANE catalytic activity in PMN media from 9 healthy donors was strongly correlated with its ability to kill MDA-MB-231 cells.

Understanding the anti-cancer function of human neutrophils through ELANE also helps explain why murine neutrophils lack this capability. Although murine ELANE kills cancer cells and murine neutrophils harbor catalytically active ELANE intracellularly and release ELANE during apoptosis, this released ELANE is not catalytically active.

Studies were performed to further determine if ECP could enhance ELANE's catalytic activity. ELANE was incubated with increasing concentrations of ECP and it was found that ECP acts as a type II allosteric activator of ELANE, wherein ECP binds ELANE with high affinity ($K_D$=17 nM) and increases its catalytic turnover (kcat) by ~12-fold. Co-immunoprecipitation experiments confirmed that ECP binds ELANE in human PMN media. These results may explain why depleting ECP from PMN media (also depletes ELANE) attenuated its killing activity, even though ECP was not toxic to cancer cells at doses present in PMN media. Furthermore, because ECP has a high affinity for biological membranes (Young et al., *Nature,* 1986), these findings may help to explain why filtration through a 0.22 μm filter selectively depleted ECP (and ELANE by association) from PMN media. Moving forward, ELANE was the focus because it is both efficacious and safe in vitro, and ECP's ability to enhance its catalytic activity could be mimicked by raising the concentration of ELANE. Indeed, higher doses of ELANE (3 μg/ml) effectively induced apoptosis in all cancer cell lines tested but were not toxic to all normal or non-cancer cells tested.

ELANE selectively kills cancer cells by cleaving CD95. How does ELANE selectively kill cancer cells? Studies focused on the CD95 pathway because it is essential for the survival of a wide range of cancer cells, but largely dispensable for normal or non-cancer cell survival (Chen et al., *Nature,* 2010), unique properties that mirrored ELANE's broad anti-cancer and low toxicity profile. Moreover, CD95 function can be modulated by proteolysis (Strand et al., *Oncogene,* 2004). Previous studies showed that lowering CD95 in cancer cells with shRNA activated a robust killing program characterized by the suppression of survival pathways, and induction of DNA damage, mitochondrial ROS (MT ROS), and effectors of apoptosis (Chen et al., *Nature,* 2010; Hadji, et al., *Cell Rep,* 2014). In contrast, this killing program was not induced in Cd95-/- normal or non-cancer cells. It was therefore hypothesized that ELANE kills cancer cells through a mechanism that involves CD95 cleavage. To begin to test this hypothesis, studies were performed to investigate whether ELANE could mimic the unique killing program caused by CD95 knockdown in cancer cells (Chen et al., *Nature,* 2010). ELANE treatment (i) suppressed at least one survival pathway (phosphorylation (p) of ERK, NFκB, or JNK), (ii) induced DNA damage (γH2AX), (iii) increased MT ROS, and (iv) activated pro-apoptotic pathways (cCASP3 and cPARP) in all 6 cancer cell lines tested (FIG. 1*a*). Consistent with its lack of toxicity to normal or non-cancer cells, ELANE did not induce this program in all normal or non-cancer cells tested (FIG. 1*a*).

Given that ELANE mimicked the killing program observed in CD95 null cancer cells, it was determined if ELANE could cleave CD95 in cancer cells, and if so, whether this resulted in loss of CD95. Cancer cells were treated with ELANE, lower molecular weight CD95 bands were observed shortly prior to cell death (FIG. 1*b*-1*c*). Although ELANE cleaved CD95 in all cancer cells tested, this cleavage did not result in loss of full-length CD95, suggesting that CD95 cleavage by ELANE may kill cancer cells through a gain-of-function and not a loss-of-function process. Consistent with this interpretation, overexpressing human CD95 (hCD95) or mouse CD95 (mCD95) in cancer cells did not protect against ELANE-mediated killing, but rather accelerated it (FIG. 1*d,* FIG. 2).

To identify ELANE cleavage sites in hCD95, recombinant proteins corresponding to the N-(aa. 1-173 of SEQ ID NO:1) or C-terminal (aa. 212-335 of SEQ ID NO:1) domains of hCD95 were incubated with ELANE. Results showed that ELANE preferentially cleaved the C-terminal domain (FIG. 1*e*), and mass spectrometric analyses identified two major cleavage sites—site 1: between $V^{220}$ and $A^{221}$, site 2: between $I^{321}$ and $Q^{332}$, resulting in the proteolytic release of the death domain (DD) of CD95 (FIG. 1*f*). Both of these sites mapped well to ELANE's sequence specificity, and studies with synthetic peptides validated these findings (FIG. 1*g*-1*h*).

Because CD95 is a plasma membrane protein and its C-terminal domain is intracellular, it was reasoned that ELANE internalization should be required for its anti-cancer function. Indeed, cancer cells rapidly internalized fluorescein-labeled ELANE, and internalized ELANE retained its catalytic activity (FIG. 1*i*-1*j*). Treatment with the endocytosis inhibitor Dynasore attenuated ELANE uptake and protected cancer cells from apoptosis (FIG. 1*j*). Dynasore also protected cancer cells from PMN media-mediated killing. Moreover, overexpressing a C-terminal domain of CD95 containing both cleavage sites (aa. 212-335 of SEQ ID NO:1) accelerated ELANE-mediated killing in both human and murine cancer cells, while over-expressing the N-terminal domain (aa 1-209 of SEQ ID NO:1) had no effect (FIG. 1*d,* FIG. 2). These results suggest that C-terminal CD95 proteolytic fragments released by ELANE cleavage may be sufficient to induce cancer cell apoptosis.

Figure 1K:
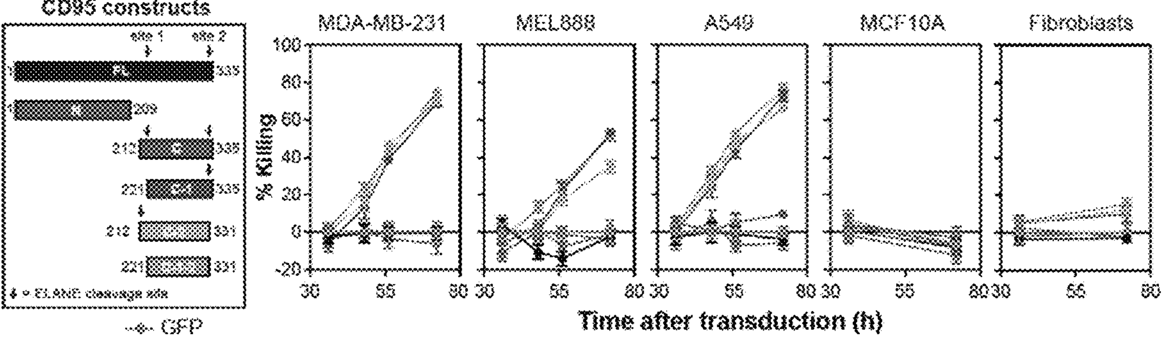
Figure 2A:
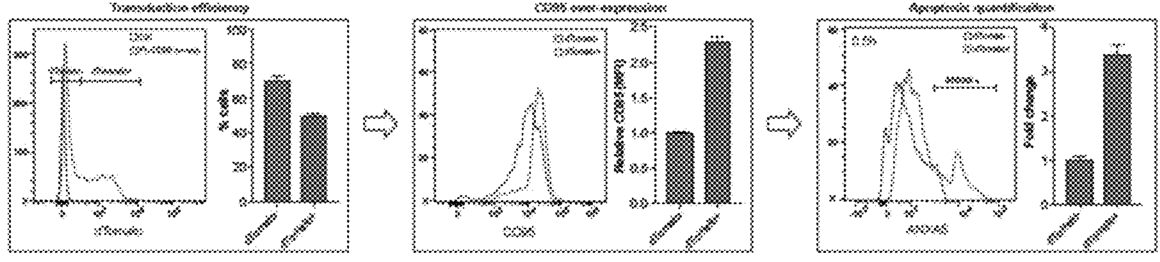
FIGS. 2A-2D Overexpressing CD95 proteins accelerates cancer cell killing by ELANE. Polycistronic adenoviral vectors were prepared to express the human and mouse CD95 sequences followed by the Encephalomyocarditis virus (EMCV) internal ribosome entry site and dTomato sequence under the control of the cytomegalovirus (CMV) promoter. Human and murine cancer cells or non-cancer cells were transduced to over-express full-length CD95, N-terminal CD95 (human: aa 1-209; mouse: aa 1-204), or C-terminal CD95 (human: aa 212-335; mouse: aa 204-327). (A): Transduction efficiency quantified by dTomato (Left). CD95 levels in dTomato− and dTomato+ cells quantified by geometric mean (MFI) (Middle). ANXA5 levels in dTomato− and dTomato+ cells 30 min after treatment with ELANE (40 nM) (Right). Representative data for A549 cells are shown. (B-C): Quantification of transduction efficiency (B) and relative CD95 overexpression (C) for cancer cells and non-cancer cells. (D): Quantification of ANXA5 levels following ELANE treatment (40 nM, 30 min) for mouse cancer cell lines (E0771, B16F10). *, $p<0.05$ Student's t-test.
Figure 2B:
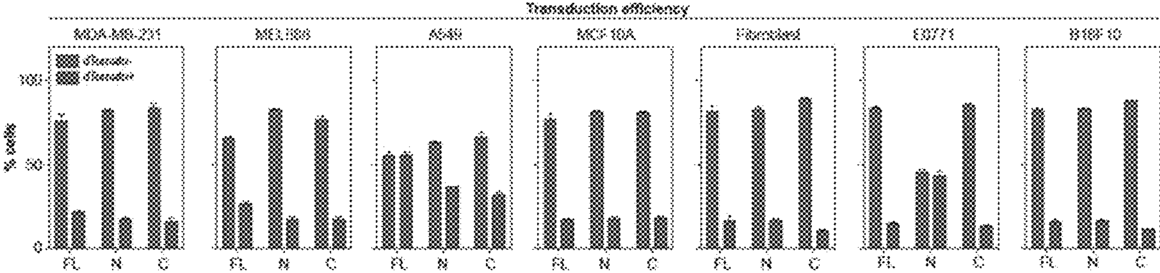
Figure 2C:
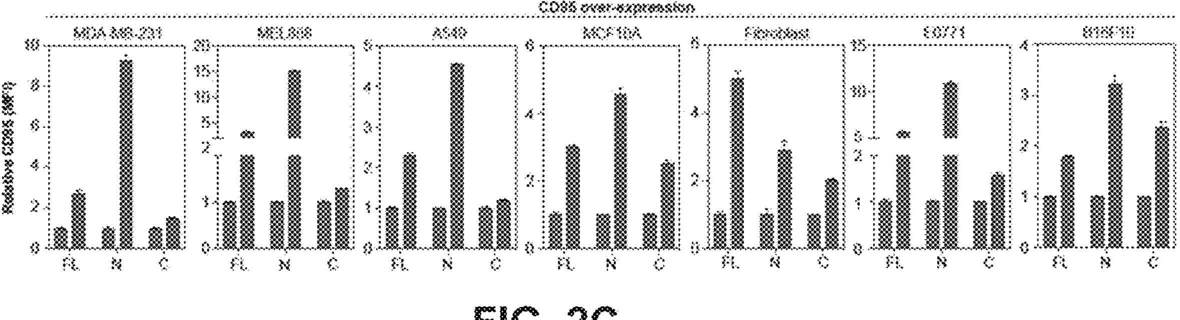
Figure 2D:
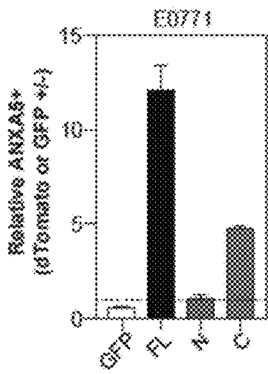
Figure 2D:
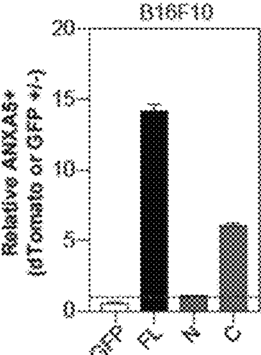

To further test this possibility, C-terminal hCD95 proteins that mimicked ELANE cleavage at site 1 (aa. 221-335 of SEQ ID NO:1), site 2 (aa. 212-331 of SEQ ID NO:1), or both sites (aa. 221-331 of SEQ ID NO:1) were overexpressed and found that expressing any of these proteins induced cancer cell death in the absence of ELANE (FIG. 1*k*). In sharp contrast, over-expressing these same C-terminal hCD95 proteins in MCF10A cells or human omental adipose tissue fibroblasts from healthy subjects did not induce toxicity (FIG. 1*k*). Thus, while normal or non-cancer cells internalize ELANE, and internalized ELANE is catalytically active, CD95 proteolytic fragments are not toxic to them (FIG. 1*a,* 1*d,* 1*i,* 1*k*). These findings reinforce the specificity of this killing mechanism to cancer cells.

IT-delivered ELANE attenuates tumorigenesis. Having shown that ELANE selectively kills cancer cells in vitro, it was investigated whether IT-delivered ELANE could attenuate tumor progression in vivo. To establish treatment conditions, various doses of ELANE were injected in an E0771 TNBC model and found that 12 μg/day gave a good therapeutic benefit that was reproducible. It was confirmed that inactivating ELANE with PMSF eliminated this therapeutic benefit, and that PMSF-ELANE did not produce unexpected worsening. Finally, it was shown that injecting ELANE (12 μg/day) into mammary fat pads of non-tumor-bearing C57BL6 mice did not produce evident side effects.

Next, the therapeutic potential of ELANE was explored in models of TNBC, lung cancer, and melanoma. Athymic nude mice were injected with MDA-MB-231, A549, or MEL888 cells (xenograft models); SCID mice with M1 or 4195 tumors (TNBC PDX models), and C57BL/6 mice with E0771, LLC1, or B16F10 cells (syngeneic models) to create tumors of ~100 $mm^3$ size. At this time, PMSF-ELANE or ELANE (12 μg/day) were injected IT and effects on tumor growth were monitored.

ELANE attenuated tumor growth in all models tested. Immunohistochemistry showed an increase in staining for TUNEL, cPARP, and cCASP3 in all ELANE-treated tumors, suggesting that ELANE induced cancer cell apoptosis in vivo. In sharp contrast, no evidence of apoptosis was found when ELANE was injected into tumor-free C57BL/6 mice. These findings are consistent with the in vitro mechanistic work, suggesting that the anti-tumor action of ELANE is both on-target and safe.

To explore whether cancer cells could acquire resistance to ELANE, a combination of in vitro and in vivo approaches were used. Repeated exposure of MDA-MB-231 cells to ELANE in vitro (7 exposures to produce ~90% death/exposure) did not confer resistance. Similarly, repeatedly treating E0771 or MEL888 tumors with ELANE in vivo (once/day for 7 days), did not attenuate ELANE's ability to kill the isolated cancer cells ex vivo. These findings suggest that developing resistance to ELANE may be challenging, which is similar to what was previously reported in CD95 knockdown cancer cells (Murmann et al., *Oncotarget,* 2017).

IT-delivered ELANE induces CD8+ T cells to attack distant tumors. The dependence of ELANE's anti-cancer function on its catalytic activity, and the abundance of serine protease inhibitors in blood restrict its therapeutic delivery to the IT route and pose a roadblock to accessing metastatic sites. This roadblock could be overcome if ELANE action on the primary tumor can induce/activate immune cells to attack tumors at distant sites, a property referred to as the abscopal effect (Ngwa et al. *Rev Cancer,* 2018).

To test this possibility, studies were performed to examine whether ELANE could increase tumor immune cells. ELANE increased the number of dendritic cells (DCs), $CD8^+$ T cells, and $CD8^+$ T effector cells ($CD8^+T_{eff}$) in all three immunocompetent models tested. Immune cell increases were not observed if ELANE was injected into mammary fat pads of tumor-free mice, nor were they observed if ELANE was injected into the contralateral site (i.e., opposite the tumor) of tumor-bearing mice, where it failed to attenuate tumorigenesis. Thus, ELANE increased innate and adaptive immune cells in tumors, and this effect was not due to an immune reaction to human ELANE.

Studies were performed to determine if treating a primary tumor with ELANE produced an immune response to decrease tumorigenesis at distant sites. E0771 cells were injected into the left (1° tumor) and right (2° tumor) mammary fat pads to create genetically identical tumors. Treating the 1° tumor with ELANE (12 μg/day for 5 days) attenuated tumorigenesis at both sites, and this effect was specific since treating a 1° E0071 tumor with ELANE did not impact tumorigenesis in a 2° B16F10 tumor, and not due to ELANE spillover. To test this in another model, a 1° B16F10 tumors were created in the flank and injected B16F10 cells into the tail vein to create 2° lung metastases. Treating the 1° tumor with ELANE (12 μg/day for 5 days) lowered the number of lung metastases. Importantly, depleting CD8+ T cells attenuated ELANE's abscopal effect in both models.

Notably, ELANE therapy produced a "crater" in ~40% of tumors in all immunocompetent models tested. Craters were not observed in tumor-free mice, nor were they observed in any immunocompromised cancer model, including C57BL/6 mice where $CD8^+$ T cells were depleted. These data suggest that ELANE-mediated cancer cell killing and the subsequent adaptive immune response, combine to create a "crater" in the tumor. However, mechanisms underlying crater development and its importance for therapeutic efficacy require further investigation.

Figure 3:
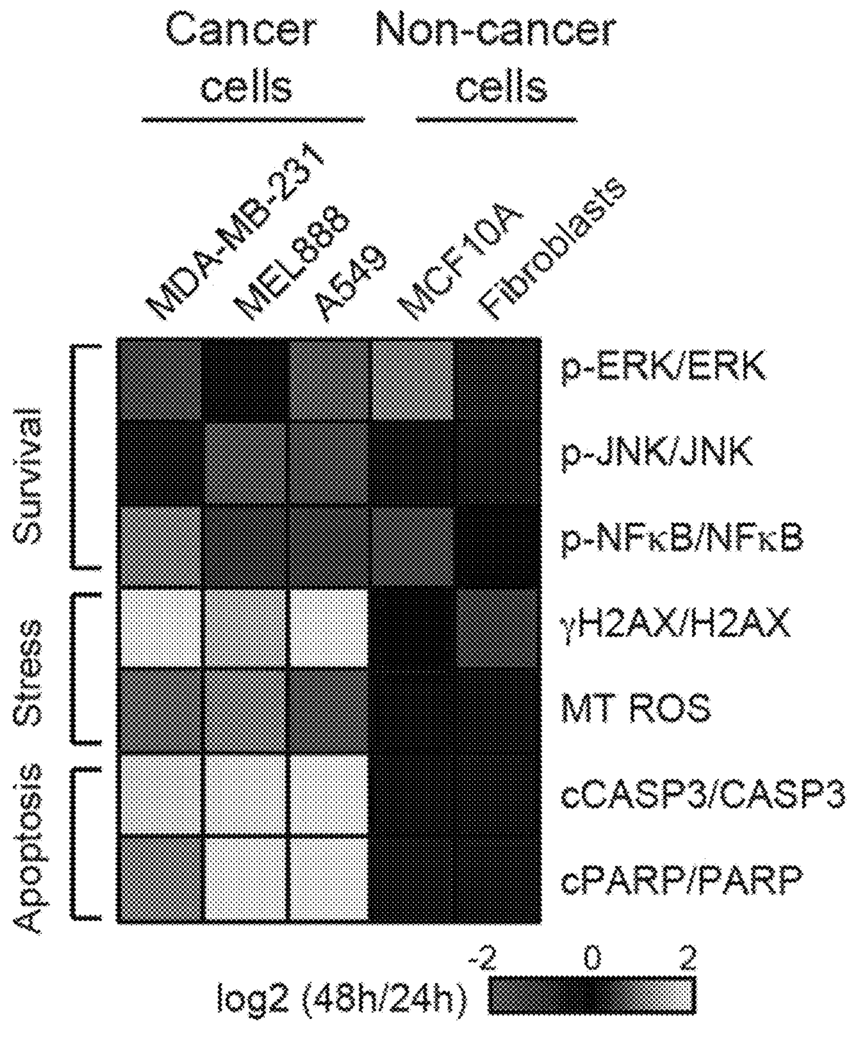
FIG. 3 Efficacy of C1-2 peptide. Heatmap of the effects C1-2 expression on survival, stress, and apoptosis pathways in cancer and non-cancer cells.
Figure 4:
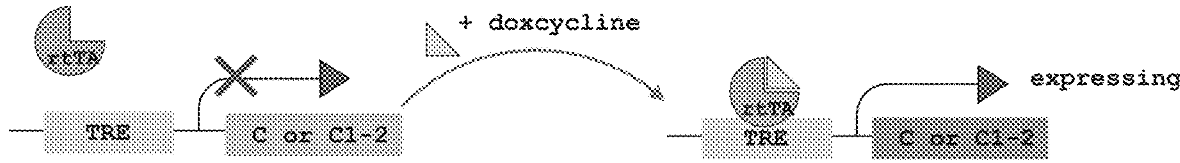
FIG. 4 Inducible Expression System. Scheme of doxycycline inducible Tet-on system to express either C (aa. 157-335) or C1-2 (aa. 221-331). C1-2 (DD containing fragment) upon addition of doxycycline (both in vitro and in vivo).
Figure 5:
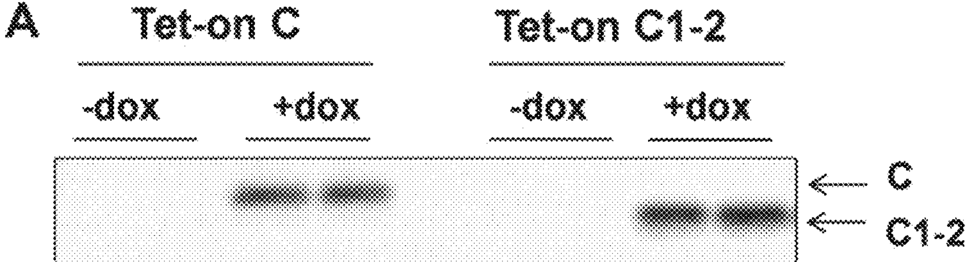
FIG. 5 Confirmation of C1-2 expression and cancer cell selective killing. (A) Tet-on C or C1-2 transduced MDA-MB-231 cells were treated with 2 μg/mL doxycycline (2 μg/mL) for 24 h. Cell lysates were collected for western blot. Confirming the expression of C or C1-2 expression. (B) Tet-on C or C1-2 transduced MDA-MB-231 cells were treated with 0.2 or 2 μg/mL doxycycline for 72 h. Cell viability was measured by Calcein AM. Expressing C1-2 not C caused MDA-MB-231 cell death. (C) Tet-on C1-2 transduced MCF10A cells were treated with 2 μg/mL doxycycline. Cell viability was measured at various time points by Calcein AM. Expressing C1-2 in MCF10A cells did not cause cell death.
Figure 5:
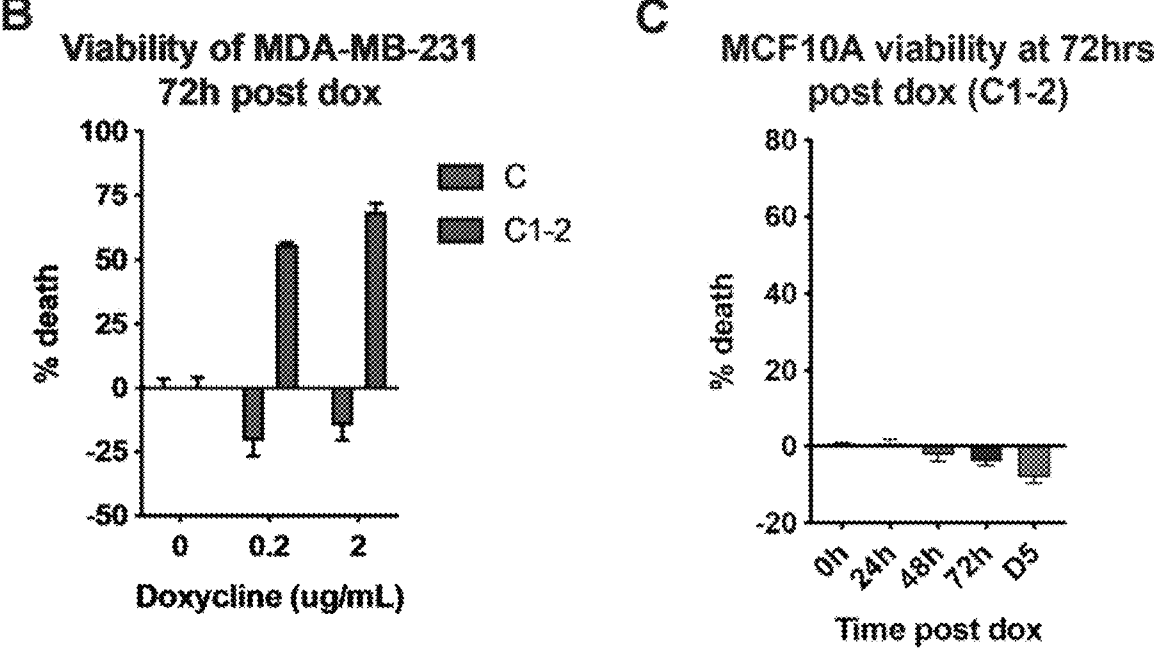
Figure 6:
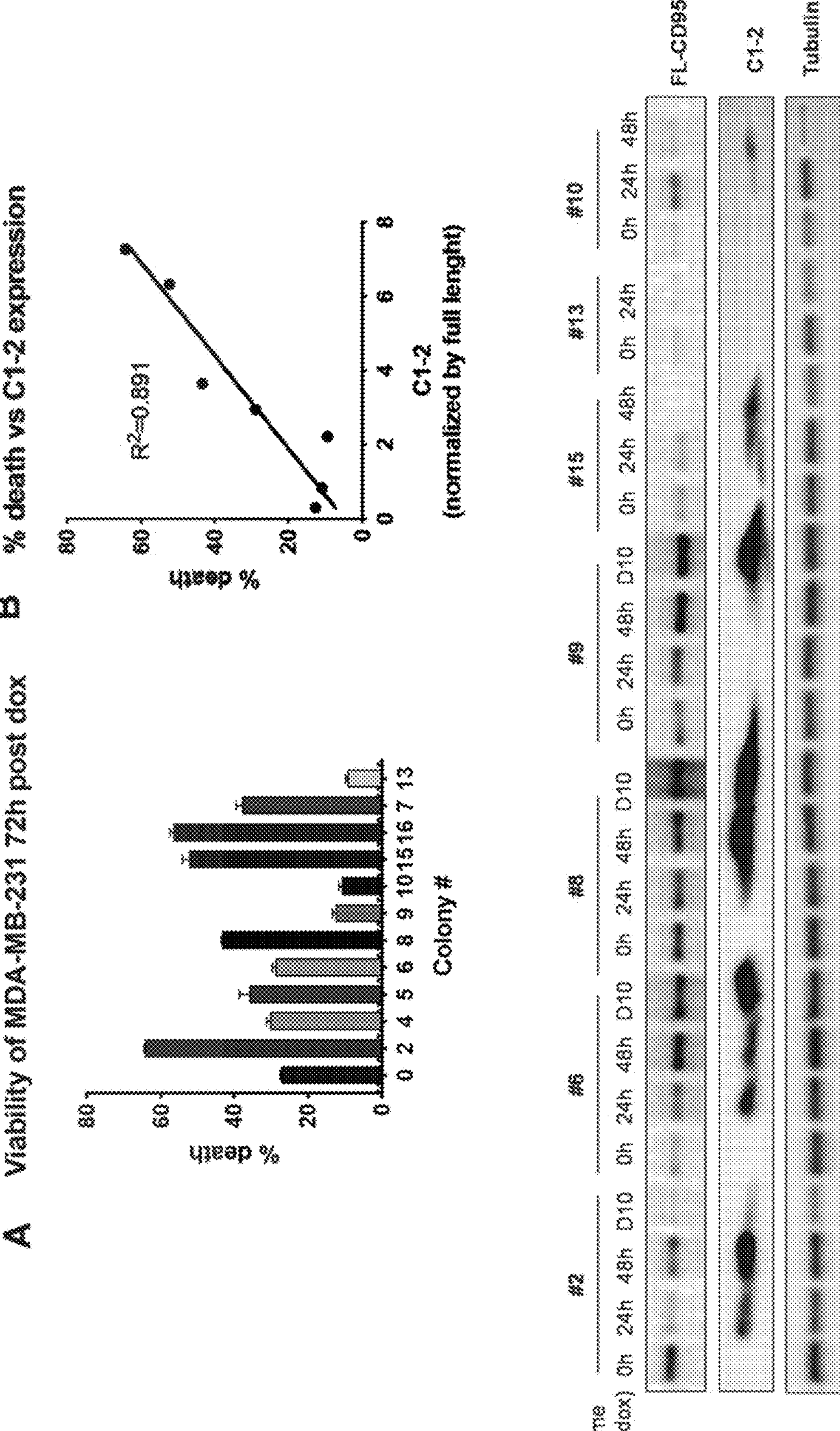
FIG. 6 In vitro testing MDA-MB-231 cell death post C1-2 induction. (A) Various single colony of Tet-on C1-2 transduced MDA-MB-231 cells were treated with 2 μg/mL doxycycline (2 μg/mL) for 72 h. Cell viability was measured by Calcein AM. Different colonies have different susceptibility of death post C1-2 induction. (B) C1-2 expression of various single colony of Tet-on C1-2 transduced MDA-MB-231 cells post doxycycline treatment were measured by western blot (C), and the level at 24 h was correlated with % death (normalized by full length). C1-2 expression correlates with MDA-MB-231 cell death. (C) Immunoblot of C1-2 and full length (FL) CD95 expression for various colony.
Figure 7:
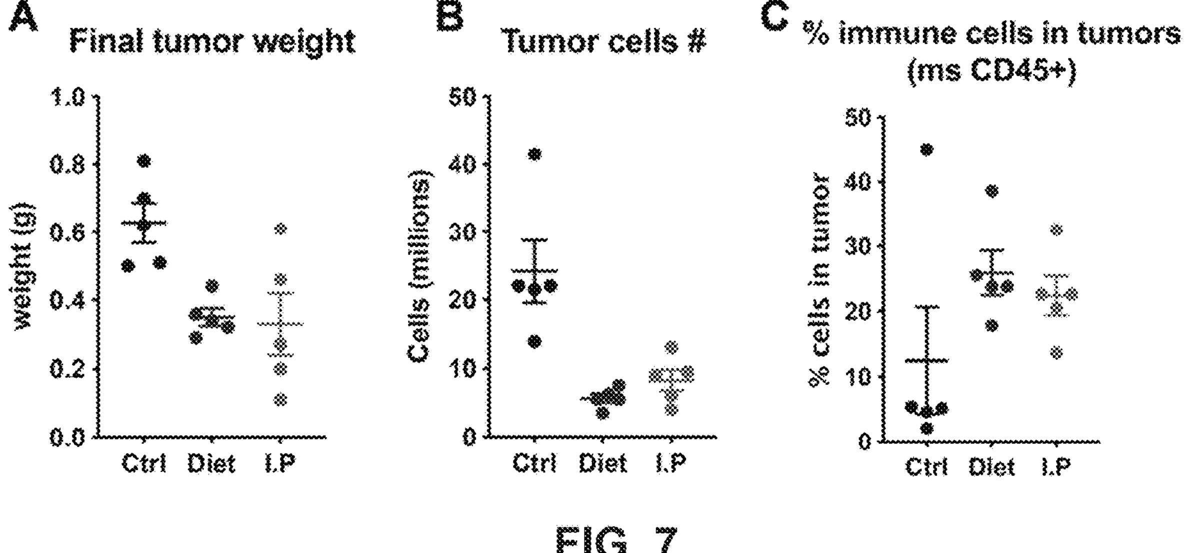
FIG. 7 In vivo testing MDA-MB-231 tumor regression post C1-2 induction. (A) Tumor weight. (B) Tumor cells (millions) count (post-ficoll gradient). (C) Percent immune cells in tumors (mouse CD45+) measurement by flow cytometry.

In vitro and In vivo Expression of Peptides. FIG. 3 illustrates effects C1-2 expression on survival, stress, and apoptosis pathways in cancer (e.g., MDA-MB-231, MEL888, and A549) and non-cancer cells (MCF10A and Fibroblasts). FIG. 4 illustrates a scheme of doxycycline inducible Tet-on system to express either C (aa. 157-335) or C1-2 (aa. 221-331). C1-2 (DD containing fragment) upon addition of doxycycline (both in vitro and in vivo). C1-2 expression can selectively kill cancer cells (FIG. 5A-5C). In vitro testing confirms C1-2 induction of cell death in MDA-MB-231 cells (FIG. 6A-6C). In vivo testing demonstrates C1-2 induced MDA-MB-231 tumor regression (FIG. 7A-7C).

B. Methods

Regulatory. Human studies were approved by the Institutional Review Board at the University of Chicago (IRB16-0321). Animal studies were approved by the Institutional Animal Care and Use Committee (ACUP72209, 72504) at the University of Chicago. Cancer cell line and viral studies were approved by the Institutional Biosafety Committee (IBC1503).

Cell lines. The ovarian cancer cell lines—CAOV3, OVCAR3, OVCAR4, OVCAR5, A2780, A2780/CP70, HeyA8, TykNu, SKOV3, ID8, and ID8p53-/- were a gift from Dr. Ernst Lengyel, University of Chicago. The breast cancer cell lines—MDA-MB-231, MDA-MB-231.BM1, MCF-7, M6C, E0771, and E0771.LMB were a gift from Dr. Marsha Rosner, University of Chicago. The colon carcinoma cell line RKO, glioblastoma cancer cell line T98G, osteosarcoma cell lines U-2OS and Saos-2, and the hepatocellular carcinoma cell line HepG2 were a gift from Dr. Kay McLeod, University of Chicago. The lung cancer cell line NCI-H552 was a gift from Dr. Stephanie Huang, University of Chicago, and A549 and LLC1 cells were purchased from ATTC. The melanoma cell lines—B16F10, Mel888, Mel1106, and SK-MEL-28 cells were a gift from Dr. Thomas Gajewski, University of Chicago. The pancreatic cancer cell line PANC1 was a gift from Dr. Yamuna Krishnan, University of Chicago. The leukemia cell line K562 was a gift from Dr. Amittha Wickrema, University of Chicago. Cells were cultured in Dubecco's Modified Eagles Medium (DMEM; HyClone) containing 10% heat-inactivated FBS (Gemini Bio Products) and 1% penicillin/streptomycin (Gibco).

The prostate cancer cell lines—CWR22Rv1, LAPC4, and LNCaP were a gift from Dr. Donald Vander Griend, University of Chicago. The neuroblastoma cell lines—SK-N-BE(2) and NBL-WN cells were a gift from Dr. Lucy Godley, University of Chicago. Cells were cultured in RPMI 1640 media (Hyclone) containing 10% heat-inactivated FBS (Gemini Bio Products) and 1% penicillin/streptomycin (Gibco).

The mammary gland epithelial cell line MCF10A was a gift from Dr. Marsha Rosner, University of Chicago. Cells were cultured in DMEM (HyClone) containing 10% heat-inactivated FBS (Gemini Bio Products), 20 ng/mL EGF (Peprotech), 0.5 mg/ml hydrocortisone (Sigma), 100 ng/mL cholera toxin (Sigma), 10 μg/mL insulin (Sigma), 1% penicillin/streptomycin (Gibco).

Primary human blood-derived cells. Human peripheral blood was donated from healthy volunteers as approved by the University of Chicago Institutional Review Committee (IRB16-0321) and following obtaining written consent. Blood was collected into EDTA-coated collection tubes (BD Vacutainer), and cells were separated with Ficoll Paque Plus (GE Healthcare) to obtain a buffy coat (containing monocytes and lymphocytes) and a bottom layer (containing neutrophils and red blood cells). Human peripheral blood neutrophils (PMNs)—PMNs were purified from the bottom layer by repetitive RBC lysis as previously described (Kuhns et al., *Curr Protoc Immunol.,* 2015). HMDMs—Monocytes were purified from the buffy coat using CD14 microbeads (MiltenylBiotec), and differentiated into HMDMs using human M-CSF (125 ng/mL, R&D Systems) as previously described (Kratz et al., *Cell Metab.,* 2014). Human Lymphocytes—Human lymphocytes were isolated from the buffy coat by collecting the flow through from CD14 and CD16 microbeads (Miltenyi Biotec). The resulting cell population was compromised of ~90% T cells and ~10% B cells.

Primary human omental fat-derived cells. Human omental adipose tissue was obtained from healthy volunteers as approved by the University of Chicago Institutional Review Board and following obtaining written consent. Human omental Neutrophils (ONs)—Omental tissue was digested with Type 1 Collagenase (Worthington, 1 mg/mL) at 37° C. with shaking at 130 rpm for 75 min to obtain stromal vascular cells (SVC). ONs were isolated from the SVC with CD16 Microbeads (Miltenyi Biotec) according to the manufacturer's protocol. Human omental fibroblasts—Human primary fibroblasts were isolated from omental adipose tissue and cultured in DMEM (HyClone) containing 20% heat-inactivated FBS (Gemini Bio Products) and 1% penicillin/streptomycin (Gibco) as previously described (Kenny at al., *Int J Cancer,* 2007).

Primary mouse cells. Unless indicated, cells were isolated from 6-8-week-old C57BL/6 mice. Murine bone marrow-derived macrophages (BMDMs)—BMDMs were differentiated from bone marrow stem cells with L-cell conditioned media as previously described (Kratz et al., *Cell Metab.,* 2014). Mouse splenocytes—Mouse splenocytes were isolated from as previously described (Reardon et al., *Cell Rep,* 2018). Resulting cells were comprised of ~5% neutrophils, ~2% monocytes, ~38% T cells, ~53% B cells. Mouse primary keratinocytes—Mouse primary keratinocytes were isolated and cultured in E low Calcein media containing 15% heat-inactivated FBS and 1% penicillin/streptomycin as previously described (Wu et al., *Cell,* 2008). Murine bone marrow-derived neutrophils (BMDNs)—BMDNs were purified using Histopaque 1119 (Sigma) and Histopaque 10771 (Sigma) density gradient centrifugation as previously described (Swamydas et al., *Curr Protoc Immunol.,* 2015). For PMA activation, BMDNs were treated with PMA (100 nM, Abcam) for 15 min, washed, and cultured for conditioned media collection. Murine thioglycolate-elicited peritoneal neutrophils (PNs)—PNs were isolated from the peritoneal cavity 7 h after 4% thioglycolate injection (3 mL/mouse, Sigma) as previously described (Swamydas et al., *Curr Protoc Immunol.,* 2015). Murine tumor-associated neutrophils (TANs)—E0771 cells were injected into the mammary fat pad of C57BL/6 mice. When tumor volume reached ~500 $mm^3$, tumors were digested with Type 4 Collagenase (Worthington, 3 mg/mL) and hyaluronidases (Sigma, 1.5 mg/mL) at 37° C. with shaking at 200 rpm for 45 min. TANs were purified with the Ly6G Microbeads (Miltenyi Biotec) according to the manufacturer's protocol. Murine lung neutrophils (LNs)—Murine LNs were isolated from 8-9-week-old MMTV-PyMT mice, a time point prior to metastatic dissemination. Lungs were digested with Liberase TL (Roche, 200 μg/mL) and DNase I (Sigma, 0.1 mg/mL) as previously described (Swamydas et al., *Curr Protoc Immunol.,* 2015). Murine LNs were purified with Ly6G Microbeads (Miltenyi Biotec) according to the manufacturer's protocol.

Neutrophil media collections. Freshly isolated human or murine neutrophils were plated in serum-free DMEM for 24 h. Conditioned media was collected, spun at 500×g for 5 min, and media protein levels were determined with a Bradford assay (Biorad).

PMN media manipulations. For boiling, PMN media was boiled at 95° C. for 5 min and spun at 15,000×g for 10 min to remove precipitated proteins. For dialysis, PMN media was placed into a Slide-a-Lyzer™ cassette (3.5 kDa cutoff, ThermoFisher Scientific) and dialyzed against 2×4L of PBS at 4° C. for 4 h. For PMSF-inactivation, PMN media was treated with PMSF (1 mM, Sigma) or A1AT (42 nM, Athens Research & Technology) and incubated at room temperature for up to 2 h. Residual PMSF was eliminated with a PD-10 desalting column (GE Healthcare Life). Inhibition of ELANE catalytic activity was confirmed using a chromogenic substrate activity assay (see below). For serum-spiking experiments, human, mouse, or fetal bovine serum (1% or 10%) was added to PMN media prior to or after exposing cancer cells. For immune-depletion studies, ELANE or ECP were immunoprecipitated using anti-ELANE (N2C3, GeneTx) or anti-ECP (MB S2535165, MyBioSource) coupled to Pierce™ Protein A/G Magnetic Beads (ThermoFisher Scientific).

In vitro cell viability assays. Cancer cells or normal or non-cancer cells were plated in complete growth media and grown to 80-90% confluence. Cells were washed with serum-free DMEM, treated with various therapeutic agents (e.g., PMN media, ELANE, etc.) for 4-24 h, and cell viability was assessed using several methods: Calcein-AM assay. 4-24 h after treatment, cells were incubated with calcein-AM (ThermoFisher Scientific, 4 ng/mL), washed with serum-free DMEM, and fluorescence was measured at 495 nm/516 nm using a Synergy HT Multi-Mode Microplate Reader (Biotek). CASP3 activity assay—Cell-associated CASP3 activity was measured 6 h after treatment using the Caspase-Glo® 3/7 Assay Systems (Promega). Luminescence was measured using a Victor X3 luminometer (PerkinElmer). ANXA5 staining—30 min—6 h after treatment, cells were stained with the FITC Annexin V Apoptosis Detection Kit (BD Pharmingen™) according to the manufacturer's protocol. Samples were analyzed using a FACSCanto™ II flow cytometer (BD Pharmingen™).

Western Blot Analysis. Cells were lysed with 1% SDS containing protease and phosphatase inhibitors (Sigma), and protein was quantified with the BCA Protein Assay Kit (Pierce). Proteins (10-20 μg) were resolved on 10%, 12.5%, 15%, or 20% SDS-PAGE gels depending on the target protein, transferred to PVDF membranes (Millipore), blocked with 5% BSA (Sigma) in 0.1% TBS/Tween-20 at RT for 2 hrs, stained with primary and secondary antibodies, and visualized using the ECL detection kit (Biorad) and a LI-COR imager. Antibodies—Antibodies against pERK (4370), ERK (4695), pNFκB (3033), NFκB (8242), pJNK (4668), JNK (9252), CASP3 (9662), PARP (9542), H2AX (2595), TUBB (2125) were from Cell Signaling Technology. Antibodies against γH2AX (05-636-I, Millipore), ELANE (68672, Abcam), N-terminal CD95 (3070R, BioVision), and C-terminal CD95 (60196, Proteintech).

Mitochondrial ROS measurements. Cells were treated with various doses of ELANE for 30 min, washed, labeled with the CM-H2DCFDA dye (ThermoFisher Scientific, 10 μM) for 30 min at 37° C., and fluorescence was quantified by flow cytometry.

CD95 overexpression studies. Polycistronic adenoviral vectors were prepared to express the human and mouse CD95 sequences followed by the Encephalomyocarditis virus (EMCV) internal ribosome entry site and dTomato sequence under the control of the cytomegalovirus (CMV) promoter (VectorBuilder). Human and murine cancer cells or normal or non-cancer cells were transduced to overexpress full-length CD95, N-terminal CD95 (human: aa 1-209; mouse: aa 1-204), C-terminal CD95 (human: aa 212-335; mouse: aa 204-327), or C-terminal CD95 that mimicked ELANE cleavage at site 1 (human: aa 221-335), site 2 (human: aa 212-331), or both sites (aa 221-331). Cancer cells or normal or non-cancer cells were transduced with adenoviruses at an MOI of 50-250 depending on cell type, and expression of dTomato and CD95 (human: 558814; mouse, mouse: 565130, BD Biosciences) were confirmed by flow cytometry. A vector encoding GFP (Vector Builders) was used as a control.

ELANE activity assays. Catalytic activity was measured using the chromogenic substrate N-Methoxysuccinyl-Ala-Ala-Pro-Val p-nitroanilide (Sigma, 100 μg/mL) according to manufacturer's protocol. Absorbance was measured at 405 nm using an accuSkan GO UV/Vis microplate spectrophotometer (ThermoFisher Scientific). For inactivation, ELANE was incubated with PMSF (1 mM, Sigma) or A1AT (42 nM, Athens Research & Technology) for 2 h. Residual PMSF was eliminated with a PD-10 desalting column (GE Healthcare Life). To monitor the effect of ECP on ELANE activity, ELANE (10 nM) was incubated with various doses of ECP (0-180 nM) at various substrate concentrations (0-1.7 mM).

Recombinant mouse ELANE activation. Recombinant mouse ELANE (50 μg/mL) was activated with CTSC (50 μg/mL) according to the manufacturer's protocol (R&D Systems).

Shotgun proteomics analyses. PMN media from 2 independent donors was passed through a 0.22 μm filter (MilliporeSigma). Pre- and post-filter media (50 μg) was digested with trypsin.

Identification of ELANE cleavage sites in CD95 by mass spectrometry. Recombinant human C-terminal CD95 (aa 212-335, MyBioSource, 10 μg) or recombinant N-terminal CD95 (aa 1-173, ThermoFisher Scientific, 10 μg) were digested with human ELANE (0.1 μg) for 2 h at 37° C., and reactions were stopped with SDS-PAGE loading buffer. Proteins were run on 20% SDS-PAGE gels, stained with Coomassie Blue (ThermoFisher Scientific), and bands were excised for mass spectrometric analyses. Proteins were extracted from excised bands.

Analysis of recombinant peptides by mass spectrometry. Recombinant peptides (10 μM) corresponding to aa 214-(TLNPETVAINLSDVDLSK)-231 (SEQ ID NO:6) or 317-(DITSDSENSNFRNEIQSLV)-335 (SEQ ID NO:7) of human CD95 (ThermoFisher Scientific) were incubated with ELANE (0.1-0.2 μM) at 37° C. for 15-30 min. Reactions were stopped with 0.1% formic acid.

Tumor inoculation and treatment. MDA-MB-231 cells ($2\times10^6$), A549 cells ($2\times10^6$) with Matrix Type 3), or MEL888 cells ($2\times10^6$ with Matrix Type 3) were injected into athymic nude mice (Charles River); M1 or 4195 cells (50,000) were injected into NOD.SCID mice (JAX); and E0771 cells ($0.5\times10^6$), LLC1 cells ($0.5\times10^6$), or B16F10 cells ($1\times10^6$), were injected into C57BL/6 mice (JAX). For TNBC models (MDA-MB-231, E0771, M1, 4195), cells were injected into the $4^{th}$ mammary fat pad of the right ventral side. For all other models (A549, LLC1, MEL888, B16F10), cells were injected into the flank. Once tumors reached ~100 mm$^3$, ELANE or PMSF-ELANE (11.6 μg/100 μL), or neutrophil medias or HSA (50 μg/100 μL) were delivered IT once/day for 5 days. Tumor volume was assessed by calipers, and experiments were terminated when tumor volume in control mice reached >1000 mm$^3$.

Tumor immunohistochemistry. Tumors were fixed in 4% paraformaldehyde in PBS for 24 h, embedded in paraffin blocks, and sectioned (5 μm). Slides were stained with cCASP3 (9661) and cPARP (9625) antibodies from Cell Signaling Technology. Signals were developed using the VECTASTAIN ABC kit (Vector Laboratories) or fluorescently-labeled secondary antibodies (melanoma models). For the TUNEL assay, staining was performed with the DeadEnd™ colorimetric or fluorometric TUNEL systems (Promega). Cell nuclei were labeled with haematoxylin or Hoechst 33342 (ThermoFisher Scientific). Images were obtained with a Nikon Eclipse Ti2 microscope and analyzed using NIS-Elements software.

Tumor immune cell analysis. Tumors were digested with Type 4 Collagenase (Worthington, 3 mg/mL) and hyaluronidases (Sigma, 1.5 mg/mL) at 37° C. with shaking at 200 rpm for 45 mins (E0771) or 30 min (LLC1 and B16F10). Cells were labeled with various antibodies and analyzed by flow cytometry. Data were quantified by FlowJo v.10.4.1. Antibodies included: CD45 (47-0451), CD11b (25-0112), MHCII (11-5321), CD4 (17-0041), CD8 (12-0081), CD44 (25-0441) from ThermoFisher Scientific; CD3 (560527), CD62L (561917), from BD Biosciences, and Ly6G (127614) from BioLegend.

Abscopal effect studies. For the E0771 model, $0.5\times10^6$ cells were injected into the $4^{th}$ mammary fat pad of the right ventral side (1° tumor) and $0.4\times10^6$ cells were injected into the $4^{th}$ mammary fat pad of the left ventral side (2° tumor) of C57BL/6 mice. Once the 1° tumor reached ~100 mm$^3$, ELANE or PMSF-ELANE (11.6 μg/100 μL) were injected IT into the 1° tumor once/day for 5 days, and 1° and 2° tumor volumes were measured by calipers. For the B16F10 model, $0.5\times10^6$ cells were injected into the flank (1° tumor). 7 days later, $0.2\times10^6$ cells were injected into the lateral tail vein to create 2° lung metastases. Once the 1° tumor reached ~100 mm$^3$, ELANE or PMSF-ELANE (11.6 μg/100 μL) were injected IT into the 1° tumor once/day for 5 days, and the 1° tumor volume was measured by calipers. Lungs were excised 10 days after the final ELANE treatment, and 2° lung metastases were counted. For CD8$^+$ T cell depletion, anti-mouse CD8α (clone 2.43, Bio X Cells) or rat IgG2b (isotype control, Bio X Cells) were injected IV (200 μg/injection) 3 days before the first ELANE treatment, and once/week after the last ELANE treatment. CD8$^+$ T cell depletion was confirmed by flow cytometry.

For the 'spillover control', $0.5\times10^6$ E0771 cells were injected into the $4^{th}$ mammary fat pad of the left ventral side (2° tumor). ELANE or PMSF-ELANE (11.6 μg/100 μL) were injected into the tumor-free $4^{th}$ mammary fat pad of the right ventral side pad once/day for 5 days, and 2° tumor volume was measured by calipers.

For the 'specificity control', $0.5\times10^6$ E0771 cells were injected into the into the $4^{th}$ mammary fat pad of the right ventral side (1° tumor) and 7 days later, $1\times10^6$B16F10 cells were injected into the flank (2° tumor). Once the 1° tumor reached ~100 mm$^3$, ELANE or PMSF-ELANE (11.6 μg/100 μL) were injected IT into the 1° tumor once/day for 5 days, and 1° and 2° tumor volumes were measured by calipers.

Assessment of potential side-effects. ELANE or PMSF-ELANE (11.6 μg/100 μL) were injected into the $4^{th}$ mammary fat pad of the right ventral side pad of tumor-free C57BL/6 mice once/day for 5 days. One day after the last injection, mice were studied for potential side-effects. Body weight and spleen weight were measured. Apoptosis at the injection site was studied by isolating, fixing, and staining mammary adipose tissue for TUNEL, cCASP3, and cPARP using identical methods described for tumors above. Mammary adipose tissue immune cell populations at the injection site were determined by flow cytometry using identical methods described for tumors above. Liver function was assessed by measuring plasma ALT activity with the Alanine Transaminase Colorimetric Activity Assays Kit (Cayman Chemical).

In Vivo testing. Mammary glands of a nude mouse model were injected with 2 million Tet-on C1-2 transduced MDA-MB-231 cells. Once tumors reach approximately 80 to 100 mm3 mice are feed either a doxycycline diet or are injected intraperitoneally with doxycycline (50 mg/ml) every 5 days to induce Tet-on system. Tumor growth is monitored. Tumors are isolated and digested on day 21 post doxycycline treatment and tumor weights are measured, tumor cell numbers are counted, and CD45+ cells are measured by flow cytometry.

Statistics. With the exception of proteomics studies, statistical significance was determined with the Student's two-tailed, unpaired t-test. Linear regression, Michaelis-Menten, and hyperbolic curve fittings were performed using Prism v.7 software.

The invention claimed is:

1. A method for treating cancer comprising administering an effective amount of a therapeutic composition comprising a peptide selected from the group consisting of SEQ ID NO:3, SEQ ID NO:4, or SEQ ID NO:5, to a subject having cancer, wherein the cancer is breast cancer, melanoma or lung cancer, wherein the therapeutic composition is administered by injection.

2. The method of claim 1, further comprising administering a second anticancer therapy, wherein the second anticancer therapy is a chemotherapy, radiotherapy, immunotherapy, or anti-hormonal therapy.

3. The method of claim 1, further comprising administering a second anticancer therapy, wherein the second anticancer therapy is an ELANE protease.

4. The method of claim 1, wherein the peptide is SEQ ID NO:3.

5. The method of claim 1, wherein the peptide is SEQ ID NO:4.

6. The method of claim 1, wherein the peptide is SEQ ID NO:5.

* * * * *